US011845776B2

(12) United States Patent
Birdsall

(10) Patent No.: US 11,845,776 B2
(45) Date of Patent: *Dec. 19, 2023

(54) MULTIDIMENSIONAL CHROMATOGRAPHY METHOD FOR ANALYSIS OF ANTIBODY-DRUG CONJUGATES

(71) Applicant: Waters Technologies Corporation, Milford, MA (US)

(72) Inventor: Robert Birdsall, Westborough, MA (US)

(73) Assignee: Waters Technologies Corporation, Milford, MA (US)

( * ) Notice: Subject to any disclaimer, the term of this patent is extended or adjusted under 35 U.S.C. 154(b) by 153 days.

This patent is subject to a terminal disclaimer.

(21) Appl. No.: 17/484,645

(22) Filed: Sep. 24, 2021

(65) Prior Publication Data

US 2022/0073561 A1 Mar. 10, 2022

Related U.S. Application Data

(63) Continuation of application No. 15/758,031, filed as application No. PCT/US2016/050628 on Sep. 8, 2016, now Pat. No. 11,149,059.

(60) Provisional application No. 62/215,339, filed on Sep. 8, 2015.

(51) Int. Cl.
*C07K 1/20* (2006.01)
*A61K 47/68* (2017.01)
*C07K 1/22* (2006.01)
*G01N 33/68* (2006.01)
*G01N 33/53* (2006.01)
*G01N 33/94* (2006.01)

(52) U.S. Cl.
CPC ............ *C07K 1/20* (2013.01); *A61K 47/6803* (2017.08); *C07K 1/22* (2013.01); *G01N 33/53* (2013.01); *G01N 33/6848* (2013.01); *G01N 33/94* (2013.01)

(58) Field of Classification Search
USPC .......................................................... 435/7.1
See application file for complete search history.

(56) References Cited

U.S. PATENT DOCUMENTS

| 5,242,824 | A | 9/1993 | Hellstrom et al. | |
| 7,989,598 | B2* | 8/2011 | Steeves | A61P 17/02 530/391.9 |
| 8,188,242 | B2 | 5/2012 | Gagnon et al. | |
| 8,202,736 | B2 | 6/2012 | Mousa et al. | |
| 8,481,694 | B2 | 7/2013 | Snyder | |
| 9,851,365 | B2 | 12/2017 | Mousa et al. | |
| 11,149,059 | B2* | 10/2021 | Birdsall | C07K 1/22 |
| 2004/0229334 | A1* | 11/2004 | Mendoza | A61P 7/02 424/94.64 |
| 2005/0048574 | A1 | 3/2005 | Kantor et al. | |
| 2005/0100967 | A1* | 5/2005 | Leslie | G01N 33/57442 435/7.1 |
| 2007/0238129 | A1 | 10/2007 | Moyer | |
| 2007/0293420 | A1* | 12/2007 | Schumann | C07K 14/505 530/412 |
| 2008/0185339 | A1 | 8/2008 | Delapierre et al. | |
| 2008/0207487 | A1* | 8/2008 | DeFrees | A61P 7/06 435/456 |
| 2008/0253992 | A1* | 10/2008 | DeFrees | C07K 1/13 435/68.1 |
| 2009/0136526 | A1 | 5/2009 | McDonagh et al. | |
| 2011/0152506 | A1* | 6/2011 | Wienand | C07K 14/505 530/397 |
| 2012/0153143 | A1* | 6/2012 | Kennedy | H01J 49/165 250/288 |
| 2014/0275494 | A1 | 9/2014 | Wang et al. | |
| 2014/0306105 | A1 | 10/2014 | Netto et al. | |
| 2015/0346170 | A1* | 12/2015 | Huang | H01J 49/0031 436/500 |
| 2016/0251441 | A1* | 9/2016 | O'Connor | C07K 16/065 530/388.15 |

FOREIGN PATENT DOCUMENTS

WO 2014006124 A1 1/2014

OTHER PUBLICATIONS

Axup, JY et al. "Synthesis of site-specific antibody-drug conjugates using unnatural amino acids." Proc Natl Acad Sci U S A. Oct. 2, 2012;109(40):16101-6.
Birdsall, RE. et al. "A rapid on-line method for mass spectrometric confirmation of a cysteine-conjugated antibody-drug-conjugate structure using multidimensional chromatography". MAbs. 2015;7(6):1036-44. doi: 10.1080/19420862.2015.1083665. Epub Aug. 25, 2015.
Burton W.G. "Separation of proteins by reversed-phase high-performance liquid chromatography. Optimizing the column" J Chromatogr. Jun. 29, 1988;443:363-79.
Chari R. V. J. et al., "Enhancement of the selectivity and antitumor efficacy of a CC-1065 analogue through Immunoconjugate formation." Cancer Res. Sep. 15, 1995;55(18):4079-84.
Chari R.V. et al. "Targeted cancer therapy: conferring specificity to cytotoxic drugs" Acc Chem Res. Jan. 2008;41(1):98-107. Epub Aug. 18, 2007.
Chen, J. et al. "Development of a native nanoelectrospray mass spectrometry method for determination of the drug-to-antibody ratio of antibody-drug conjugates." Anal Chem. Feb. 5, 2013;85(3):1699-704. doi: 10.1021/ac302959p. Epub Jan. 18, 2013.
Clardy J. et al. "Lessons from natural molecules." Nature. Dec. 16, 2004;432(7019):829-37.
Cohen SA. et al., "Multiple Peak Formation in Reversed-Phase Liquid Chromatography of Papain" Anal. Chem., 1984, 56 (2), pp. 217-221.

(Continued)

Primary Examiner — Ann Montgomery
(74) Attorney, Agent, or Firm — WOMBLE BOND DICKINSON (US) LLP; Deborah M. Vernon

(57) ABSTRACT

The present disclosure relates to a sensitive, multidimensional chromatography method for extraction, detection, and quantification of non-conjugated cytotoxic agents and associated linker molecules used in cysteine based antibody-drug-conjugate production.

5 Claims, 10 Drawing Sheets

(56) References Cited

OTHER PUBLICATIONS

Debaene F. et al. "Innovative native MS methodologies for antibody drug conjugate characterization: High resolution native MS and IM-MS for average DAR and DAR distribution assessment." Anal Chem. Nov. 4, 2014;86(21):10674-83. doi: 10.1021/ac502593n. Epub Oct. 21, 2014.
Doronina, SO et al. "Development of potent monoclonal antibody auristatin conjugates for cancer therapy." Nat Biotechnol. Jul. 2003;21(7):778-84.
Dosio F. et al. "Immunotoxins and anticancer drug conjugate assemblies: the role of the linkage between components." Toxins (Basel). Jul. 2011;3(7):848-83. doi: 10.3390/toxins3070848.
Fleming MS. et al. "A reversed-phase high-performance liquid chromatography method for analysis of monoclonal antibody-maytansinoid immunoconjugates." Anal Biochem. May 15, 2005;340(2):272-8.
Francisco J.A. et al. "CAC10-vcMMAE, an anti-CD30-monomethyl auristatin E conjugate with potent and selective anti-tumor activity" Blood. Aug. 15, 2003;102(4):1458-65. Epub Apr. 24, 2003.
Green J.M "A Practical Guide to Analytical Method Validation" Anal. Chemi., 1996, 68 (9), pp. 305A-309A, DOI: 10.1021/ac961912f, Publication Date (Web): May 24, 2011.
Greenfield RS et al. "Evaluation in vitro of adriamycin immunoconjugates synthesized using an acid-sensitive hydrazone linker." Cancer Res. Oct. 15, 1990;50(20):6600-7.
He Y. et al. "On-line coupling of size exclusion chromatography with mixed-mode liquid chromatography for comprehensive profiling of biopharmaceutical drug product." J Chromatogr A. Nov. 2, 2012;1262:122-9. doi: 10.1016/j.chroma.2012.09.012.
Hofer, T et al. "Molecularly defined antibody conjugation through a selenocysteine interface." Biochemistry. Dec. 22, 2009:48(50):12047-57.
Huang RY. et al. "Utility of Ion Mobility Mass Spectrometry for Drug-to-Antibody Ratio Measurements in Antibody-Drug Conjugates." J Am Soc Mass Spectrom. Oct. 2015;26(10):1791-4. doi: 10.1007/s13361-015-1203-1. Epub Jun. 30, 2015.
Hudecz F. et al., "The influence of synthetic conditions on the stability of methotrexate-monoclonal antibody conjugates determined by reversed phase high performance liquid chromatography." Biomed Chromatogr. May-Jun. 1992;6 (3):128-32.
Hurwitz E. et al. "The covalent binding of daunomycin and adriamycin to antibodies, with retention of both drug and antibody activities." Cancer Res. May 1975;35(5):1175-81.
International Search Report and Written Opinion for International Application No. PCT/US2016/050628, competed on Oct. 19, 2016 and dated Dec. 9, 2016 (15 Pages).
Janin-Bussat M.C. et al. "Characterization of antibody drug conjugate positional isomers at cysteine residues by peptide mapping LC-MS analysis." J Chromatogr B Analyt Technol Biomed Life Sci. Feb. 15, 2015;981-982:9-13. doi: 10.1016/j.jchromb.2014.12.017. Epub Dec. 24, 2014.
Jeong CK. et al., "Narrowbore high-performance liquid chromatography for the simultaneous determination of sildenafil and its metabolite UK-103,320 in human plasma using column switching." J Chromatogr B Biomed Sci Appl. Mar. 5, 2001,752(1):141-7.
Junutula JR et al. "Site-specific conjugation of a cytotoxic drug to an antibody improves the therapeutic index." Nat Biotechnol. Aug. 2008;26(8) 925-32. doi: 10.1038/nbt.1480.
King R. et al. "Mechanistic investigation of ionization suppression in electrospray ionization." J Am Soc Mass Spectrom. Nov. 2000;11(11):942-50.
Kovtun YV. et al. "Antibody-drug conjugates designed to eradicate tumors with homogeneous and heterogeneous expression of the target antigen." Cancer Res. Mar. 15, 2006,66(6):3214-21.
Kozak KR. et al., "Total antibody quantification for MMAE-conjugated antibody-drug conjugates: impact of assay format and reagents." Bioconjug Chem. May 15, 2013;24(5):772-9. doi: 10.1021/bc300491k.
Lazar A.C. et al. "Analysis of the composition of immunoconjugates using size-exclusion chromatography coupled to mass spectrometry" Rapid Commun Mass Spectrom. 2005;19(13):1806-14.
Lee HM. et al. "Microbore high-performance liquid chromatographic determination of cisapride in rat serum samples using column switching." J Chromatogr B Biomed Sci Appl. Apr. 30, 1999;727(1-2):213-7.
Lewis Phillips GD et al. "Targeting HER2-Positive Breast Cancer with Trastuzumab-DM1, Antibody-Cytotoxic Drug Conjugate." Cancer Res Nov. 15, 2008, 2008;68(22):9280-9290. Downloaded from cancerres.aacrjournals.org on Mar. 11, 2015. Ó 2008 American Association for Cancer Research.
Li Y. et al. "A size exclusion-reversed phase two dimensional-liquid chromatography methodology for stability and small molecule related species in antibody drug conjugates." J Chromatogr A. May 8, 2015;1393:81-8. doi: 10.1016/j.chroma.2015.03.027.
Li Y. et al. "Characterization and stability study of polysorbate 20 in therapeutic monoclonal antibody formulation by multidimensional ultrahigh-performance liquid chromatography-charged aerosol detection-mass spectrometry." Anal Chem. May 20, 2014,86(10):5150-7. doi: 10.1021/ac5009628.
Li Y. et al. "Limiting degradation of reactive antibody drug conjugate intermediates in HPLC method development." J Pharm Biomed Anal. Apr. 2014;92:114-8. doi: 10.1016/j.jpba.2014.01.004.
Liu M. et al., "HPLC method development, validation and impurity characterization for an antitumor Hsp90 inhibitor-PU-H71 (NSC 750424)." J Pharm Biomed Anal. Feb. 2014; 89:34-41. doi: 10.1016/j.jpba.2013.10.021.
McDonagh, CF et al. "Engineered antibody-drug conjugates with defined sites and stoichiometries of drug attachment." Protein Eng Des Sel. Jul. 2006;19(7):299-307.
Pascoe R. et al. "Reduction in matrix-related signal suppression effects in electrospray ionization mass spectrometry using on-line two-dimensional liquid chromatography." Anal Chem. Dec. 15, 2001;73(24):6014-23.
Pro B et al. "Five-year results of brentuximab vedotin in patients with relapsed or refractory systemic anaplastic large cell lymphoma." Blood. Dec. 21, 2017;130(25):2709-2717.
Reichert, JM et al. "Monoclonal antibody successes in the clinic." Nat Biotechnol. Sep. 2005;23(9):1073-8.
Remillard S. et al. "Antimitotic activity of the potent tumor inhibitor maytansine" Science. Sep. 19, 1975,189 (4207):1002-5.
Sanderson RJ. et al. "In vivo drug-linker stability of an anti-CD30 dipeptide-linked auristatin immunoconjugate." Clin Cancer Res. Jan. 15, 2005;11(2 Pt 1):843-52.
Shen B.Q. et al. "Conjugation site modulates the in vivo stability and therapeutic activity of antibody-drug conjugates" Nat Biotechnol. Jan. 22, 2012;30(2):184-9. doi: 10.1038/nbt.2108.
Singtoroj T. et al. "A new approach to evaluate regression models during validation of bioanalytical assays" J Pharm Biomed Anal. Apr. 11, 2006;41(1):219-27. Epub Dec. 5, 2005.
Souverain S. et al. "Restricted access materials and large particle supports for on-line sample preparation: an attractive approach for biological fluids analysis." J Chromatogr B Analyt Technol Biomed Life Sci. Mar. 5, 2004;801 (2):141-56.
Stephan JP et al., "Challenges in developing bioanalytical assays for characterization of antibody-drug conjugates." Bioanalysis. Mar. 2011;3(6):677-700. doi: 10.4155/bio.11.30.
Stoll D.R. et al. "Comparison of the practical resolving power of one- and two-dimensional high-performance liquid chromatography analysis of metabolomic samples" Anal Chem. Jan. 1, 2008;80(1):268-78. Epub Dec. 6, 2007.
Stoll, DR. et al. "Direct identification of rituximab main isoforms and subunit analysis by online selective comprehensive two-dimensional liquid chromatography-mass spectrometry." Anal. Chem., 2015, 87(16), pp. 8307-8315, Jul. 6 epub.
Strebhardt K. et al. "Paul Ehrlich's magic bullet concept: 100 years of progress" Nat Rev Cancer. Jun. 2008;8 (6):473-80. doi: 10.1038/nrc2394. Epub May 12, 2008.
Sun MM et al. "Reduction-alkylation strategies for the modification of specific monoclonal antibody disulfides." Bioconjug Chem. Sep.-Oct. 2005;16(5):1282-90.

(56) References Cited

OTHER PUBLICATIONS

Thorson J.S. "Understanding and exploiting nature's chemical arsenal: the past, present and future of calicheamicin research" Curr Pharm Des. Dec. 2000; 6(18):1841-79.

Valliere-Douglass J.F. "Approaches to Interchain Cysteine-Linked ADC Characterization by Mass Spectrometry" Mol Pharm. Jun. 1, 2015; 12(6):1774-83. doi: 10.1021/mp500614p. Epub Dec. 17, 2014.

Valliere-Douglass, J. et al. "Separation of populations of antibody variants by fine tuning of hydrophobic-interaction chromatography operating conditions." J Chromatogr A. Dec. 19, 2008;1214(1-2):81-9. doi: 10.1016/j.chroma.2008.10.078. Epub Oct. 25, 2008.

Valliere-Douglass, JF. et al. "Native intact mass determination of antibodies conjugated with monomethyl Auristatin E and F at interchain cysteine residues." Anal Chem. Mar. 20, 2012;84(6):2843-9. doi: 10.1021/ac203346c. Epub Mar. 2, 2012.

Vega-Morales T., et al. "Development and optimisation of an on-line solid phase extraction coupled to ultra-high-performance liquid chromatography-tandem mass spectrometry methodology for the simultaneous determination of endocrine disrupting compounds in wastewater samples". Journal of Chromatography A vol. 1230, Mar. 23, 2012, pp. 66-76.

Wagner-Rousset E et al. "Antibody-drug conjugate model fast characterization by LC-MS following IdeS proteolytic digestion." MAbs. Jan.-Feb. 2014;6(1):173-84.

Wakankar A. et al. "Analytical methods for physicochemical characterization of antibody drug conjugates" MAbs. Mar.-Apr. 2011;3(2):161-72. Epub Mar. 1, 2011.

Wu, A. et al. "Arming antibodies: prospects and challenges for immunoconjugates." Nat Biotechnol. Sep. 2005,23 (9):1137-46.

Xu et al. "Characterization of intact antibody-drug conjugates from plasma/serum in vivo by affinity capture capillary liquid chromatography-mass spectrometry." Anal. Biochem. 412(2011): 56-66.

Zhang K. et al. "Analysis of pharmaceutical impurities using multi-heartcutting 2D LC coupled with UV-charged aerosol MS detection." J Sep Sci. Sep. 2013;36(18):2986-92. doi: 10.1002/jssc.201300493. Epub Jul. 31, 2013.

\* cited by examiner

Fluorophore (DSEA)
Chemical Formula: C₂₀H₃₀N₄O₃S; Exact Mass: 406.2

Maleimide-Linker-Fluorophore (Mal-linker-DSEA)
Chemical Formula: C₅₀H₆₈N₁₀O₁₁S; Exact Mass: 1004.5

Quenched-Linker-Fluorophore (NAc-linker-DSEA)
Chemical Formula: C₅₄H₇₇N₁₁O₁₅S₂; Exact Mass: 1167.5

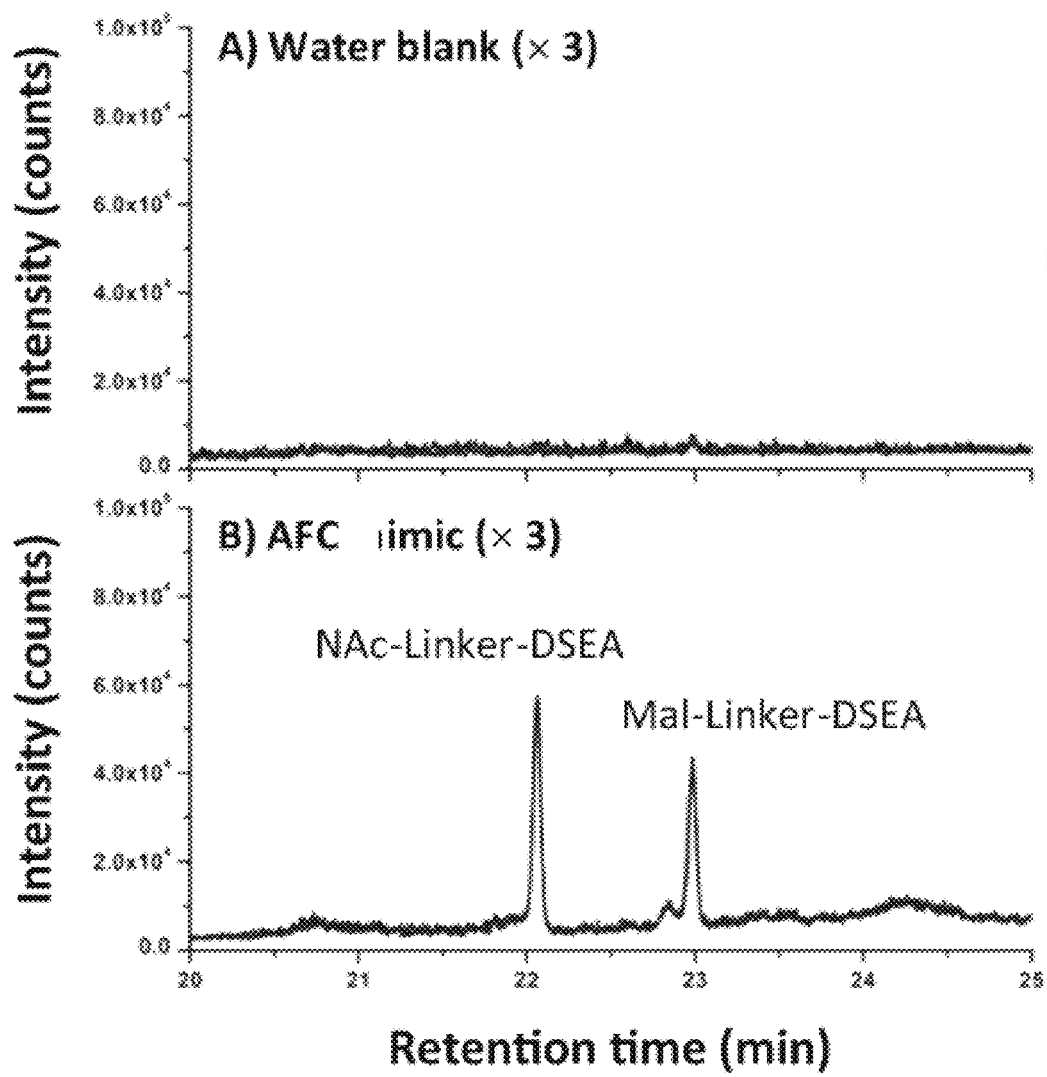

MULTIDIMENSIONAL CHROMATOGRAPHY METHOD FOR ANALYSIS OF ANTIBODY-DRUG CONJUGATES

CROSS-REFERENCE TO RELATED APPLICATIONS

This application is a continuation of U.S. application Ser. No. 15/758,031, filed Mar. 7, 2018 which is a National Stage Application of International Application No. PCT/US2016/050628, filed Sep. 8, 2016, which claims priority to U.S. Provisional Application No. 62/215,339, filed Sep. 8, 2015. Each of the foregoing applications is incorporated herein by reference in its entirety.

FIELD OF THE INVENTION

The present disclosure relates to a sensitive, multidimensional chromatography method for extraction, detection, and quantification of non-conjugated cytotoxic agents and associated linker molecules used in cysteine based antibody-drug-conjugate production.

BACKGROUND

Antibody-drug conjugate (ADC) compounds represent a growing class of immunoconjugate therapies. ADC compounds are complex molecules composed of a monoclonal antibody connected to a biologically active, highly cytotoxic drug via a cleavable (e.g., acid labile linkers, protease cleavable linkers, and disulfide linkers) or a non-cleavable linker. The conjugation of potent drugs to a monoclonal antibody enables the targeted delivery of toxic payloads to tumor surfaces while minimizing systemic toxicity effects to healthy tissue, thus improving the therapeutic window for such modalities in the treatment of cancer.

Incomplete conjugation processes can result in free or non-conjugated drug, drug-linker, or drug related impurities. Additionally, degradation products can occur over time in formulation as well as in vivo, increasing the risk to patients and reducing the efficacy of the ADC compound. Trace levels of these free drug species may be present in formulated ADC compounds despite purification steps implemented during the production process. For these reasons, characterization of residual free drug and associated products is required to ensure a safe and efficacious product.

Current methods for the detection of trace free drug species are ultimately encumbered by several drawbacks, including low specificity and/or sensitivity in the detection, characterization, and quantification of trace free drug species in unadulterated ADC compound samples. Accordingly there remains a need in the art for new detection methods that enable straightforward integration into existing or novel workflows.

SUMMARY OF THE INVENTION

The present disclosure relates to new and useful multidimensional chromatography methodologies for detecting and/or quantifying one or more non-conjugated drugs (e.g., cytotoxic and anticancer compounds) and associated linker molecules used in the production of cysteine-based antibody-drug conjugate compounds.

Accordingly, provided herein is a method for analyzing antibody-drug conjugate compounds in samples comprising an antibody-drug conjugate compound and an unconjugated drug compound. The method includes the steps of exposing the sample to a first dimension comprising a mixed mode stationary phase and exposing the sample to a second dimension comprising hydrophobic stationary phase. The method provides for separation of the antibody-drug conjugate compound and the unconjugated drug compound in the sample.

In some embodiments, the method further comprises the step of trapping the unconjugated drug compound. In one embodiment, the trapping step is performed prior to the step of exposing the sample to the first dimension. Alternatively, the trapping step is performed between the step of exposing the sample the first dimension and the step of exposing the sample to the second dimension.

Also provided herein is a method analyzing antibody-drug conjugate compounds in samples comprising an antibody-drug conjugate compound, an unconjugated drug compound, and an associated linker molecule. In some embodiments, the unconjugated drug compound is the free drug. In other embodiments, the unconjugated drug compound is linked to a reactive form of the associated linker molecule. In still other embodiments, the unconjugated drug compound is linked to a quenched or deactivated form of the linker molecule. The sample is first exposed to a first dimension separation, then the sample is exposed to a second dimension separation. The method involves the step of trapping a portion of the unconjugated drug compound and/or the associated linker molecule with a stationary phase either prior to the first dimension separation or between the first dimension separation and the second dimension separation.

The methods provided herein detect each of the antibody-drug conjugate compound, the unconjugated drug compound, and, optionally, the associated linker molecule in the samples of the methods. In some embodiments, mass spectrometry is used to detect each of the antibody-drug conjugate compound, the unconjugated drug compound, and, optionally, the associated linker molecule in the samples of the method. In particular embodiments, the methods provided herein use mass spectrometry to establish a mass to charge ratio of each of the antibody-drug conjugate compound, the unconjugated drug compound, and, optionally, the associated linker molecule in the samples of the methods. In other embodiments, ultraviolet and/or visible spectroscopy is used to detect each of the antibody-drug conjugate compound, the unconjugated drug compound, and, optionally, the associated linker molecule in the samples of the method. In still other embodiments, fluorescence spectroscopy is used to detect each of the antibody-drug conjugate compound, the unconjugated drug compound, and, optionally, the associated linker molecule in the samples of the method.

BRIEF DESCRIPTION OF THE DRAWINGS

FIGS. 10A-B depict the DSEA sample. A) using the optimized 2DLC method as shown in FIG. 7, a water blank was performed prior to each DSEA sample injection to monitor carry-over between DSEA sample injections. Overlay chromatograms of the three water blanks indicate negligible carry over of mal-linker-DSEA and no observable carry over of NAc-linker-DSEA between runs. B) mal-linker-DSEA and NAc-linker-DSEA drug components were detected in a 10 μL injection (19.4 μg) of neat AFC sample. Overlays of the three runs indicate a high degree of assay reproducibility.

DETAILED DESCRIPTION OF THE INVENTION

Figure 1:
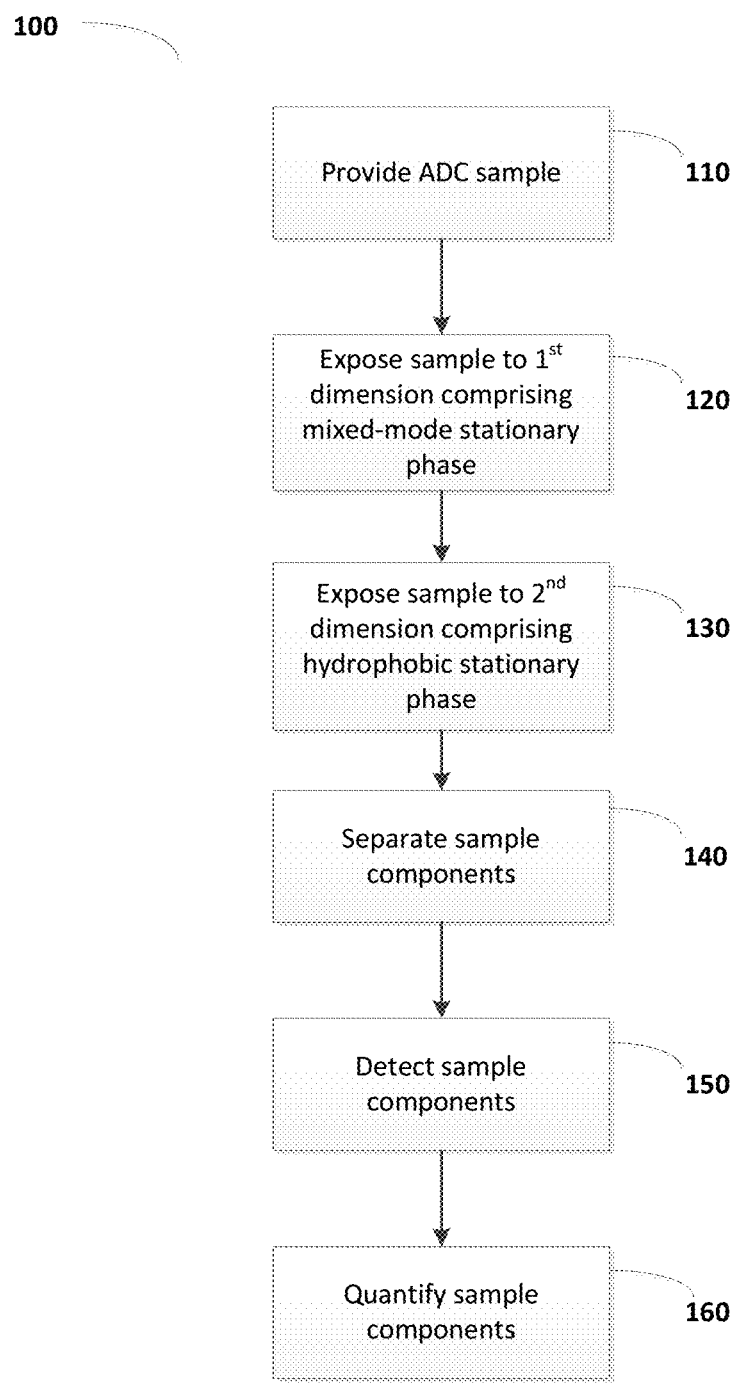
FIG. 1 shows one exemplary embodiment of the method of the invention.

Reference will now be made in detail to certain embodiments of the invention, examples of which are illustrated in the accompanying figures. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described.

Definitions

Unless stated otherwise, the following terms and phrases as used herein are intended to have the following meanings:

As used herein "antibody drug conjugates: or "ADCs" are monoclonal antibodies (mAbs) attached to biologically active drugs by chemical linkers with labile bonds.

"Antibody" is used herein in the broadest sense and specifically covers monoclonal antibodies, polyclonal antibodies, multispecific antibodies (e.g., bispecific antibodies), and antibody fragments. Antibodies may be murine, human, humanized, chimeric, or derived from other species. An antibody is a protein generated by the immune system that is capable of recognizing and binding to a specific antigen. (Janeway, et al (2001) "*Immunobiology*", 5th Ed., *Garland Publishing*, New York). A target antigen generally has numerous binding sites, also called epitopes, recognized by CDRs on multiple antibodies. Each antibody that specifically binds to a different epitope has a different structure. Thus, one antigen may have more than one corresponding antibody.

Antibody also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "linker unit" refers to the direct or indirect linkage of the antibody to the drug. Attachment of a linker to a mAb can be accomplished in a variety of ways, such as through surface lysines, reductive-coupling to oxidized carbohydrates, and through cysteine residues liberated by reducing interchain disulfide linkages. A variety of ADC linkage systems are known in the art, including hydrazone-, disulfide- and peptide-based linkages. The term "active pharmaceutical ingredient" or "API" refers to is the ingredient in a pharmaceutical drug that is biologically active. The terms "pharmaceutical drug," "drug," and "payload" are used interchangeably throughout, and refer to any substance having biological or detectable activity, for example, therapeutic agents, detectable labels, binding agents, etc., and prodrugs, which are metabolized to an active agent in vivo.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z").

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), ultra-high performance liquid chromatography (UHPLC), turbulent flow liquid chromatography (TFLC) (sometimes known as high turbulence liquid chromatography (HTLC) or high throughput liquid chromatography).

As used herein, the term "high performance liquid chromatography" or "HPLC" (also sometimes known as "high pressure liquid chromatography") refers to liquid chromatography in which the degree of separation is increased by forcing the mobile phase under pressure through a stationary phase, typically a densely packed column. As used herein, the term "ultra high performance liquid chromatography" or "UHPLC" (sometimes known as "ultra high pressure liquid chromatography") refers to HPLC that occurs at much higher pressures than traditional HPLC techniques.

The term "LC/MS" refers to a liquid chromatograph (LC) interfaced to a mass spectrometer.

Methods of the Invention

The present disclosure relates to new and useful multidimensional chromatography methodologies for detecting and/or quantifying one or more non-conjugated drugs (e.g., cytotoxic and anticancer compounds) and associated linker molecules used in the production of cysteine-based antibody-drug conjugate compounds.

Figure 2:
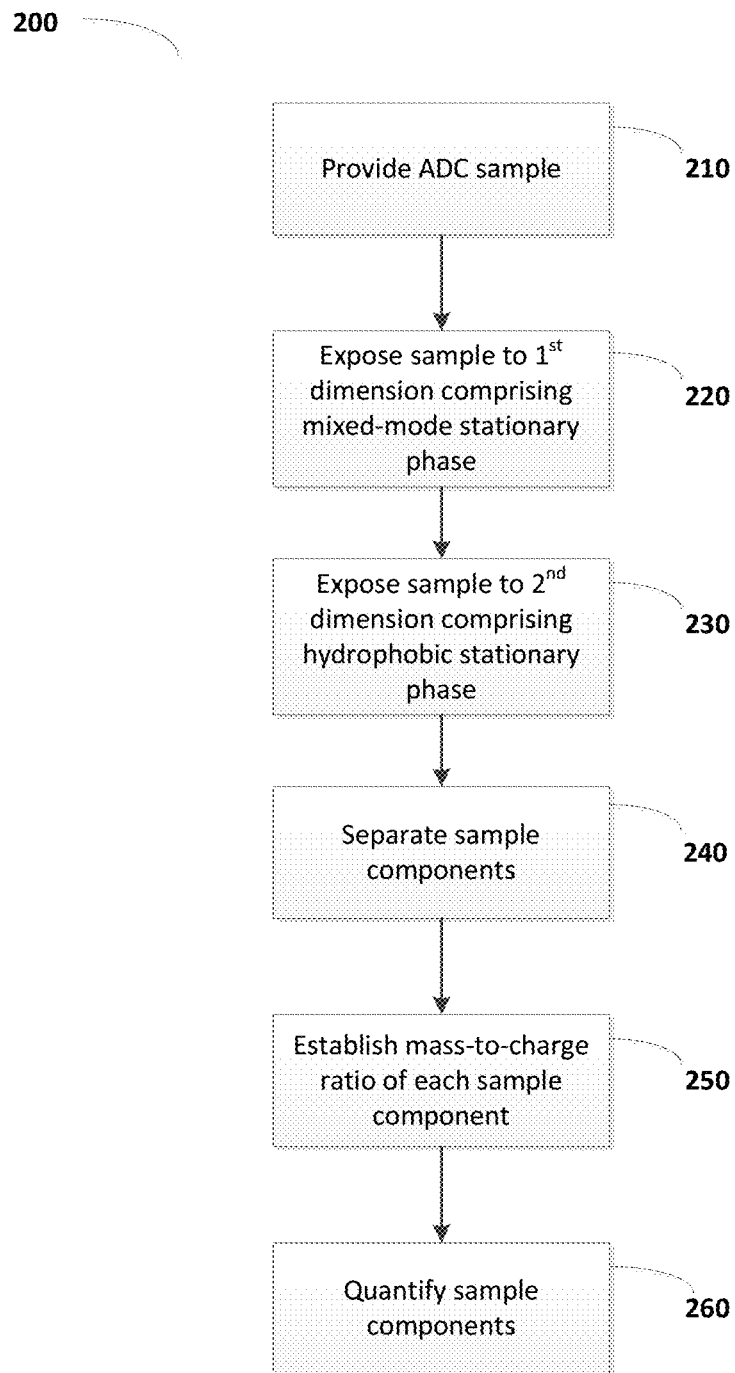
FIG. 2 shows one exemplary embodiment of the method of the invention.

Accordingly, as shown in FIGS. 1 and 2, provided herein are methods (100, 200) for analyzing antibody-drug conjugate compounds in samples comprising an antibody-drug conjugate compound and an unconjugated drug compound. The methods include the steps of exposing the sample to a first dimension comprising a mixed mode stationary phase (120, 220) and exposing the sample to a second dimension comprising hydrophobic stationary phase (130, 230). The methods provide for separation (140, 240) of the antibody-drug conjugate compound and the unconjugated drug compound in the sample.

In some embodiments, some of the methods further comprise the step of trapping the unconjugated drug compound. In one embodiment, the trapping step is performed prior to the step of exposing the sample to the first dimension. Alternatively, the trapping step is performed between the step of exposing the sample the first dimension and the step of exposing the sample to the second dimension.

Figure 3:
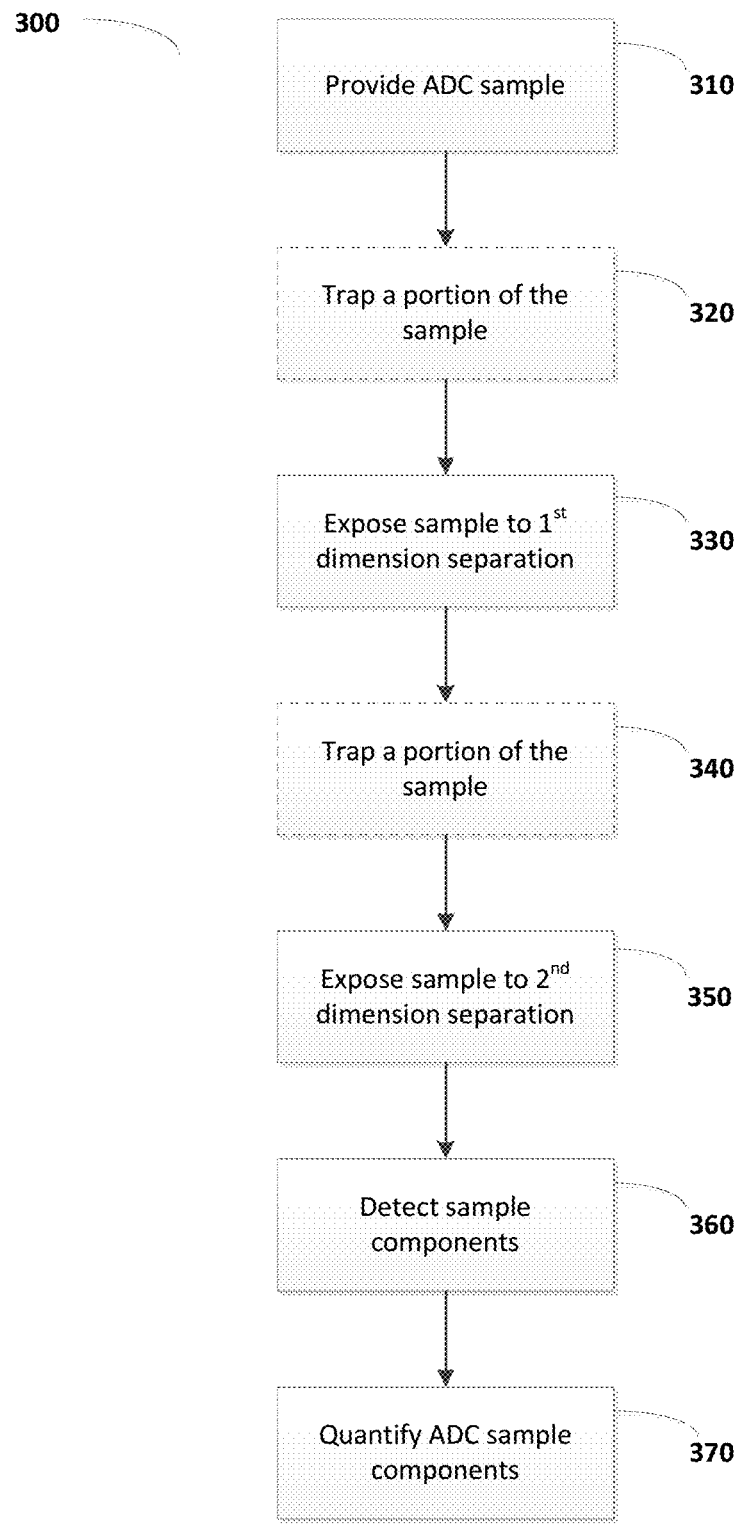
FIG. 3 shows one exemplary embodiment of the method of the invention.

As shown in FIG. 3, also provided herein is a method (300) analyzing antibody-drug conjugate compounds in samples comprising an antibody-drug conjugate compound, an unconjugated drug compound, and an associated linker molecule. In some embodiments, the unconjugated drug compound is the free drug. In other embodiments, the unconjugated drug compound is linked to a reactive form of the associated linker molecule. In still other embodiments, the unconjugated drug compound is linked to a quenched or deactivated form of the linker molecule. The sample is first exposed to a first dimension separation (330), then the sample is exposed to a second dimension separation (350). The method involves the step of trapping a portion of the unconjugated drug compound and/or the associated linker molecule with a stationary phase either prior to the first dimension separation (320) or between the first dimension separation and the second dimension separation (340).

As shown in FIG. 1, the methods provided herein detect (150) each of the antibody-drug conjugate compound, the unconjugated drug compound, and, optionally, the associated linker molecule in the samples of the methods. In some embodiments, mass spectrometry is used to detect each of the antibody-drug conjugate compound, the unconjugated drug compound, and, optionally, the associated linker molecule in the samples of the method. As shown in FIG. 2, in particular embodiments, the methods provided herein use mass spectrometry to establish a mass to charge ratio (250) of each of the antibody-drug conjugate compound, the unconjugated drug compound, and, optionally, the associated linker molecule in the samples of the methods. In other embodiments, ultraviolet and/or visible spectroscopy is used to detect each of the antibody-drug conjugate compound, the unconjugated drug compound, and, optionally, the associated linker molecule in the samples of the method. In still other embodiments, fluorescence spectroscopy is used to detect each of the antibody-drug conjugate compound, the unconjugated drug compound, and, optionally, the associated linker molecule in the samples of the method.

Figure 4A:
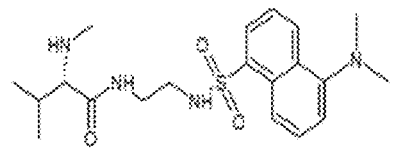
FIGS. 4A-C depict antibody-fluorophore-conjugate (AFC) mimic components. Drug components used in the production of a non-toxic AFC to mimic chemistry and linker species of brentuximab vedotin were based on a A) dansyl sulfonamide ethyl amine (DSEA) moiety attached to B) a maleimidocaproyl valine-citrulline linker species (Mal-linker-DSEA). Residual reactive mal-linker-DSEA was quenched with N-acetyl-cysteine following the conjugation step, producing a C) quenched-linker-fluorophore (NAc-linker-DSEA) adduct species.
Figure 4B:
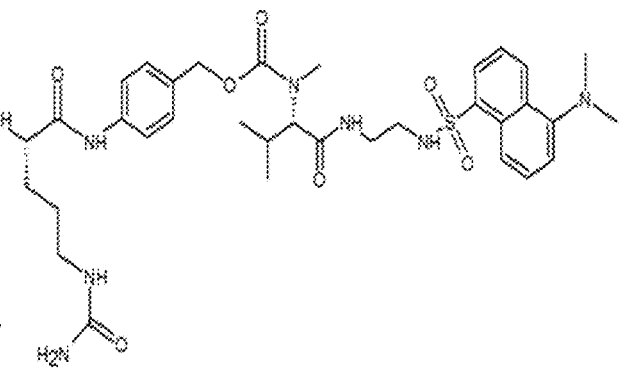
Figure 4C:
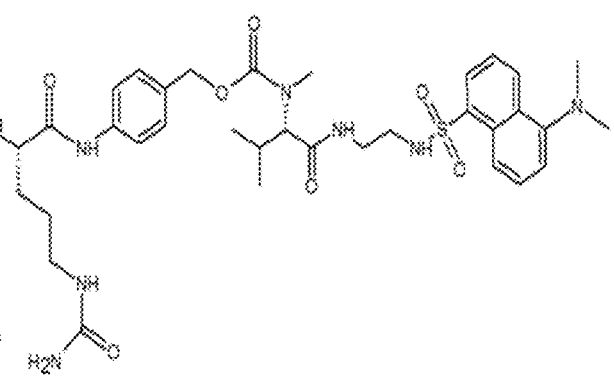

In some embodiments, an antibody-fluorophore-conjugate (AFC) mimic is used (FIG. 4). Such a non-toxic AFC can be used to mimic chemistry and linker species of, for example, brentuximab vedotin, and as such the "drug" components may be based on a dansyl sulfonamide ethyl amine (DSEA) moiety (FIG. 4A) attached to a maleimidocaproyl valine-citrulline linker species (Mal-linker-DSEA) (FIG. 4B). Residual reactive mal-linker-DSEA can be quenched with N-acetyl-cysteine following the conjugation step, producing a quenched-linker-fluorophore (NAc-linker-DSEA) adduct species (FIG. 4C).

These methods provided herein are particularly useful for quantifying the low levels (e.g., ng/mL) of unconjugated drug compound in said samples.

The present methods offer several advantages over the prior art. For example, the present methods bypass the need to precipitate protein, and require substantially no sample preparation (e.g., no pre-concentration, buffer exchanges, or dilutions). Additionally, there is no carryover of protein or biological matrix constituents, which can compromise detection and quantification results. The disclosed method also extends the linear dynamic range, which thereby increases the operating specification range that can be performed.

1$^{st}$ Dimension

The 1$^{st}$ dimension column should be able to separate or resolve the protein or antibody from the free drug components with sufficient resolution between the two species to allow the drug to be sent to a trap or 2$^{nd}$ dimension column while directing the protein component to waste. This is performed by exploiting the physicochemical properties of the ADC. An example for mixed mode is the net charge contrast of the antibody with the free drug molecules. Size-exclusion chromatography or SEC exploits the size difference between a large antibody and the small drug species.

In one embodiment, the 1$^{st}$ dimension is a mixed mode anion exchanger. Therewith, net positive proteins pass through the column under acidic conditions while the net neutral to basic drugs are adsorbed to the column stationary phase for later elution.

In another embodiment, the 1$^{st}$ dimension is a mixed mode cation exchanger. Therewith, positively charged proteins are retained while allowing drug species to pass with the injection void to be captured by a trap or 2$^{nd}$ dimension column.

In yet another embodiment, the 1$^{st}$ dimension is size exclusion chromatography. Therewith, large antibodies pass to waste isocratically with early elution times while small drug molecules elute later in the total inclusion peak or post total inclusion peak due to secondary interactions with the stationary phase.

In one embodiment, the 1$^{st}$ dimension column is an on-line 2.1×20 mm, 30 micron solid phase extraction column (Oasis® MAX available from Waters Technologies Corporation, Milford, MA). Therewith, both trapping and first dimensional separation occur within this column.

2$^{nd}$ Dimension Column

The 2$^{nd}$ dimension column should be designed to minimize pressure on the 1$^{st}$ dimension if the 1$^{st}$ dimension column cannot tolerate high pressure. As an example, an embodiment using an OASIS® column (available from Waters Technology Corporation Milford, MA) as the 1$^{st}$ dimension separation; the pressure of this 1$^{st}$ dimension column should not exceed more than 6,000 PSI. Factors that effect pressure are column length (shorter=lower pressure), size of particle (larger particle=lower pressure), flow rate (low flow=lower pressure), column inner diameter (large inner diameter=lower pressure), and temperature (higher temp=lower pressure). However, a balance of these parameters found as short, large particle, wide bore columns can result in decrease chromatographic performance. Accordingly, in one embodiment, the disclosed methods use a superficially porous small particle 50 mm Cortecs column. In some embodiments, the second dimension column is a 2.1×50 mm, 2.7 micron superficially porous C18 column (Cortecs® C18 available from Waters Technologies Corporation, Milford, MA).

If not limited by the 1$^{st}$ dimension column, however, the 2$^{nd}$ dimension column can be of any dimensions and stationary phase that exhibits enough retentivity to retain the drug species after at-column-dilution is performed and result in an acceptable separation of the drug components. Nonetheless, columns that are too retentive may result in carryover of trace protein, lengthy elution times, and/or poor chromatography of hydrophobic drug species.

Organic Modifier and Acid %

Hydrophobic active pharmaceutical ingredients (APIs) require optimization of elution strength of organic solvent. Under low acid concentration conditions, more hydrophobic analytes may not elute completely or may be too broad to elute in a defined window. Higher acid concentration conditions allows drug species to elute in an acceptable window.

In some embodiments, neat organic solvent or in mixed compositions with increasing elution strength is used to elute more hydrophobic drug species from the 1$^{st}$ dimension. For drug components that are too hydrophilic or elute under relatively mild organic compositions, the initial organic composition when injected can be lowered to retain those species, and a two-step gradient can be employed to capture the less hydrophobic species with the more hydrophobic species.

In other embodiments, the acid % is modified at injection to use lower acid % at injection to retain the more hydrophilic species, then increase to the 2% acid composition to elute all drug components. This may be accomplished by using an additional solvent line(s) on the quaternary solvent manager, e.g., a pump.

Exemplary solvents that can be used in the disclosed methods include, but are not limited to, water, acetonitrile, ammonium acetate, ammonium formate, methanol, ethanol, isopropanol, propanol, tetrahydrofuran, and combinations thereof Exemplary acids that can be used in the disclosed methods include, but are not limited to, acetic acid, formic acid, difluoroacetic acid, and trifluoroacetic acid.

Transfer of the Drug Components

The mechanism of transferring the drug components to an analytical 2$^{nd}$ dimensions can either be performed using a trap column or at-column-dilution.

When using at-column-dilution, the goal is to dilute the strong eluting solvent composition % to facilitate the adsorption of eluting drug components onto the head of the 2$^{nd}$ dimension column. If the organic composition is too high, the drugs if adsorbed could result in peak splitting or reduced chromatographic performance, or worst case scenario, be passed through the column without being retained and result in in-accurate assessment of drug levels. Adjusting the flow rate of the 2$^{nd}$ dimension pump allows for proper dilution. An example would be if the drug eluted from the 1$^{st}$ dimension at 50% organic at a constant flow rate of 0.100 ml/min and the desired organic composition for re-adsorption in the 2$^{nd}$ dimension column was 25% then the method would flow 0.100 mL/min from the 2$^{nd}$ dimension pump to effectively dilute the sample in a 1:1 ratio.

In some embodiments, a trap is used. Therewith, the trap should be retentive enough to retain eluting drug species and in all likelihood at-column-dilution would still have to be used. Additionally, the trap should have equal or lower retentivity than the 2$^{nd}$ dimension column. If the trap were more retentive than the 2$^{nd}$ dimension column, then the analyte(s) would elute off the trap in a mobile phase composition that does not favor adsorption to the 2$^{nd}$ dimension column, and the 2$^{nd}$ dimension column would not add additional separation benefits. The use of the trap can help lower pressure exposure on the 1$^{st}$ dimension column and allows the method to be performed at higher flow rates and shorter run times.

Linker and Drug Type

In one embodiment, the methods disclosed herein use an ADC mimic with a fluorophore conjugate, which exhibits a lower hydrophobic characteristic than an ADC comprising a commercial API, as demonstrated by Li et al. [*J Chromatogr A*. 2015; 1393:81-8] For more hydrophobic drug species, the organic percent and acid concentration may be modified in a manner similar to a more hydrophobic API, as discussed above. Likewise, if an increased organic composition is required to elute the API components, the at-column-dilution and retentivity of the $2^{nd}$ dimension can be modified accordingly.

The methods disclosed herein may be applied to non-cleavable linkers and/or pH labile linkers.

In one embodiment, the present methods can be used to analyze a cysteine-conjugated ADCs. Alternatively, the present methods can be used to analyze lysine conjugated ADCs. Cysteine-conjugated ADCs typically have a relatively low drug load (e.g., 0-8 drugs). In contrast, lysine-conjugated ADCs typically have a higher drug load (e.g., 1-10 or more drugs). The lysine-conjugated ADCs may exhibit a higher degree of hydrophobicity due to (1) increased drug load and (2) the fact the inter-chain disulfide bonds are still intact. If the increased hydrophobicity results in protein material being retained on the $1^{st}$ dimension and subsequently being eluted to the $2^{nd}$ dimension column, than it may be appropriate to cleave the conjugated drugs prior to analysis at which point the cleaved species will generate a unique mass distinguishable from the free drug components. By cleaving the drugs the hydrophobicity of the antibody is reduced allowing it to be passed through the $1^{st}$ dimensions column as designed while retaining cleaved drug and free-drug. If the protein is still too hydrophobic than addition of a reducing agent to reduce the inter-chain disulfides may be used to reduce the intact antibody into its respective sub-units.

Detection Techniques

Methods of the present technology include one or more detection or detecting steps. For example, some embodiments utilize mass spectrometry for detection of the antibody-drug conjugate compound and the unconjugated drug compound in the sample. In some embodiments, mass spectrometry is used to establish a mass to charge ratio of each of the antibody-drug conjugate compound and the unconjugated drug compound in the sample.

In certain other embodiments, optical spectroscopy is used as the preferred detection technique. In a particular embodiment, ultraviolet (UV) and/or visible spectroscopy is used.

Mass Spectrometry

A variety of mass spectrometry systems capable of high mass accuracy, high sensitivity, and high resolution are known in the art and can be employed in the methods of the invention. The mass analyzers of such mass spectrometers include, but are not limited to, quadrupole (Q), time of flight (TOF), ion trap, magnetic sector or FT-ICR or combinations thereof. The ion source of the mass spectrometer should yield mainly sample molecular ions, or pseudo-molecular ions, and certain characterizable fragment ions. Examples of such ion sources include atmospheric pressure ionization sources, e.g. electrospray ionization (ESI) and Matrix Assisted Laser Desorption Ionization (MALDI). ESI and MALDI are the two most commonly employed methods to ionize proteins for mass spectrometric analysis. ESI and APC1 are the most commonly used ion source techniques for LC/MS (Lee, M. "LC/MS Applications in Drug Development" (2002) *J. Wiley & Sons*, New York).

Surface Enhanced Laser Desorption Ionization (SELDI) is an example of a surface-based ionization technique that allows for high-throughput mass spectrometry (U.S. Pat. No. 6,020,208). Typically, SELDI is used to analyze complex mixtures of proteins and other biomolecules. SELDI employs a chemically reactive surface such as a "protein chip" to interact with analytes, e.g., proteins, in solution. Such surfaces selectively interact with analytes and immobilize them thereon. Thus, the analytes of the invention can be partially purified on the chip and then quickly analyzed in the mass spectrometer. By providing different reactive moieties at different sites on a substrate surface, throughput may be increased.

Commercially available mass spectrometers can sample and record the whole mass spectrum simultaneously and with a frequency that allows enough spectra to be acquired for a plurality of constituents in the mixture to ensure that the mass spectrometric signal intensity or peak area is quantitatively representative. This will also ensure that the elution times observed for all the masses would not be modified or distorted by the mass analyzer and it would help ensure that quantitative measurements are not compromised by the need to measure abundances of transient signals.

Optical Spectroscopy

A variety of optical spectroscopy systems capable of high accuracy, high sensitivity, and high resolution are known in the art and can be employed in the methods of the invention. Absorption spectroscopy refers to optical spectroscopic techniques that measure the absorption of radiation, as a function of frequency or wavelength, due to its interaction with a sample. The sample absorbs energy, i.e., photons, from the radiating field. The intensity of the absorption varies as a function of frequency, and this variation is the absorption spectrum. Absorption spectroscopy is performed across the electromagnetic spectrum.

Absorption spectroscopy is employed as an analytical chemistry tool to determine the presence of a particular substance in a sample and, in many cases, to quantify the amount of the substance present. Infrared and ultraviolet-visible spectroscopy are particularly common in analytical applications.

There are a wide range of experimental approaches for measuring absorption spectra. The most common arrangement is to direct a generated beam of radiation at a sample and detect the intensity of the radiation that passes through it. The transmitted energy can be used to calculate the absorption. The source, sample arrangement and detection technique vary significantly depending on the frequency range and the purpose of the experiment.

The most straightforward approach to absorption spectroscopy is to generate radiation with a source, measure a reference spectrum of that radiation with a detector and then re-measure the sample spectrum after placing the material of interest in between the source and detector. The two measured spectra can then be combined to determine the material's absorption spectrum. The sample spectrum alone is not sufficient to determine the absorption spectrum because it will be affected by the experimental conditions—the spectrum of the source, the absorption spectra of other materials in between the source and detector and the wavelength dependent characteristics of the detector. The reference spectrum will be affected in the same way, though, by these experimental conditions and therefore the combination yields the absorption spectrum of the material alone.

A wide variety of radiation sources can be employed in order to cover the electromagnetic spectrum. For spectroscopy, it is generally desirable for a source to cover a broad swath of wavelengths in order to measure a broad region of the absorption spectrum. Some sources inherently emit a broad spectrum. Examples of these include globars or other black body sources in the infrared, mercury lamps in the visible and ultraviolet and x-ray tubes. One recently developed, novel source of broad spectrum radiation is synchrotron radiation which covers all of these spectral regions. Other radiation sources generate a narrow spectrum but the emission wavelength can be tuned to cover a spectral range. Examples of these include klystrons in the microwave region and lasers across the infrared, visible and ultraviolet region (though not all lasers have tunable wavelengths).

The detector employed to measure the radiation power will also depend on the wavelength range of interest. Most detectors are sensitive to a fairly broad spectral range and the sensor selected will often depend more on the sensitivity and noise requirements of a given measurement. Examples of detectors common in spectroscopy include heterodyne receivers in the microwave, bolometers in the millimeter-wave and infrared, mercury cadmium telluride and other cooled semiconductor detectors in the infrared, and photodiodes and photomultiplier tubes in the visible and ultraviolet.

UV/Visible Spectroscopy

"Ultraviolet/visible spectroscopy" refers to absorption spectroscopy or reflectance spectroscopy in the ultraviolet (UV) and/or visible electromagnetic spectral region.

Ultraviolet (UV) electromagnetic radiation can have a wavelength ranging from 100 nm (30 PHz) to 380 nm (750 THz), shorter than that of visible light but longer than X-rays. The visible light is a type of electromagnetic radiation that is visible to the human eye. Visible electromagnetic radiation can have a wavelength ranging from about 390 nm (430 THz) to about 700 nm (770 THz).

The instrument used in ultraviolet-visible spectroscopy is called a UV/Vis spectrophotometer. It measures the intensity of light passing through a sample (I), and compares it to the intensity of light before it passes through the sample ($I_o$). The ratio $I/I_o$, is called the transmittance, and is usually expressed as a percentage (% T). The absorbance, A, is based on the transmittance:

Fluorescence Spectroscopy

"Fluorescence spectroscopy" refers to a type of electromagnetic spectroscopy that analyzes fluorescence from a sample. It involves using a beam of light, usually ultraviolet light, that excites the electrons in molecules of certain compounds and causes them to emit light; typically, but not necessarily, visible light. A complementary technique is absorption spectroscopy. In the special case of single molecule fluorescence spectroscopy, intensity fluctuations from the emitted light are measured from either single fluorophores, or pairs of fluorophores.

Two general types of instruments exist: (1) filter fluorometers that use filters to isolate the incident light and fluorescent light; and (2) spectrofluorometers that use a diffraction grating monochromators to isolate the incident light and fluorescent light. Both types use the following scheme: the light from an excitation source passes through a filter or monochromator, and strikes the sample. A proportion of the incident light is absorbed by the sample, and some of the molecules in the sample fluoresce. The fluorescent light is emitted in all directions. Some of this fluorescent light passes through a second filter or monochromator and reaches a detector, which is usually placed at 90° to the incident light beam to minimize the risk of transmitted or reflected incident light reaching the detector.

Various light sources may be used as excitation sources, including lasers, LED, and lamps; xenon arcs and mercury-vapor lamps in particular. A laser only emits light of high irradiance at a very narrow wavelength interval, typically under 0.01 nm, which makes an excitation monochromator or filter unnecessary. A mercury vapor lamp is a line lamp, meaning it emits light near peak wavelengths. By contrast, a xenon arc has a continuous emission spectrum with nearly constant intensity in the range from 300-800 nm and a sufficient irradiance for measurements down to just above 200 nm.

Filters and/or monochromators may be used in fluorimeters. A monochromator transmits light of an adjustable wavelength with an adjustable tolerance. The most common type of monochromator utilizes a diffraction grating, that is, collimated light illuminates a grating and exits with a different angle depending on the wavelength. The monochromator can then be adjusted to select which wavelengths to transmit. For allowing anisotropy measurements the addition of two polarization filters are necessary: One after the excitation monochromator or filter, and one before the emission monochromator or filter.

As mentioned above, the fluorescence is most often measured at a 90° angle relative to the excitation light. This geometry is used instead of placing the sensor at the line of the excitation light at a 180° angle in order to avoid interference of the transmitted excitation light. No monochromator is perfect and it will transmit some stray light, that is, light with other wavelengths than the targeted. An ideal monochromator would only transmit light in the specified range and have a high wavelength-independent transmission. When measuring at a 90° angle, only the light scattered by the sample causes stray light. This results in a better signal-to-noise ratio, and lowers the detection limit by approximately a factor 10000, when compared to the 180° geometry. Furthermore, the fluorescence can also be measured from the front, which is often done for turbid or opaque samples.

The detector can either be single-channeled or multichanneled. The single-channeled detector can only detect the intensity of one wavelength at a time, while the multichanneled detects the intensity of all wavelengths simultaneously, making the emission monochromator or filter unnecessary. The different types of detectors have both advantages and disadvantages.

The most versatile fluorimeters with dual monochromators and a continuous excitation light source can record both an excitation spectrum and a fluorescence spectrum. When measuring fluorescence spectra, the wavelength of the excitation light is kept constant, preferably at a wavelength of high absorption, and the emission monochromator scans the spectrum. For measuring excitation spectra, the wavelength passing though the emission filter or monochromator is kept constant and the excitation monochromator is scanning. The excitation spectrum generally is identical to the absorption spectrum as the fluorescence intensity is proportional to the absorption.

INCORPORATION BY REFERENCE

The contents of all references, patents and published patent applications cited throughout this application, as well as the Figures, are hereby incorporated by reference in their entirety.

Exemplification

Having described the invention, the same will be more readily understood through reference to the following Example, which is provided by way of illustration, and are not intended to limit the invention in any way.

Example 1: A Targeted Multidimensional Method (SPE-RPLC/MS) for the Assessment of Trace Free Drug Species in Unadulterated Antibody-Drug Conjugate (ADC) Samples Using Mass Spectral Detection for Improved Specificity and Sensitivity This example uses an SPE-RPLC/MS approach that is specific, sensitive, and enables method control in two dimensions. The method was evaluated using a clinically relevant valine-citrulline surrogate molecule based on brentuximab vedotin. Assay sensitivity was found to be two orders more sensitive using MS detection in comparison to UV based detection with an LOQ of 0.30 ng/mL. Free-drug species were present in an unadulterated ADC surrogate sample at concentrations below 7.0 ng/mL, levels not detectable by UV alone. The 2DLC method provides a high degree of specificity and sensitivity in the assessment of trace free drug species with improved control over each dimension enabling straightforward integration into existing or novel workflows.

Results:

The selection of an ADC for this example that offers the broadest applicability of the proposed method and exhibits a pH stable linker molecule is preferred. For ease of use and handling, an ADC that exhibits negligible or no cytotoxicity while closely approximating the characteristics of commercial ADCs is equally desirable. To this end, an antibody-fluorophore-conjugate (AFC), as previously described [Wagner-Rous set, E., et al., mAbs, 2014. 6(1): p. 173-184] was used for this study. Key aspects in the design of the AFC were that it mimic physiochemical characteristics of the clinically relevant ADC brentuximab vedotin (Adcetris®) [Pro, B., et al. *Journal of Clinical Onocology*, 2012. 30(18): p. 2190-2196; Francisco, J. A., et al. *Blood*, 2003. 102(4): p. 1458-1465], minimize cytotoxicity through the use of a non-cytotoxic drug mimic, and have minimal impact on the integrity of the original ADC. Substitution of mono-methylauristatin E (MMAE) with a dansyl sulfonamide amine (DSEA, FIG. 1A) while maintaining the maleimidocaproyl valine-citrulline linker (mal-linker-DSEA, FIG. 1B), which is actively used in ADCs, successfully meets these criteria. An in-depth study of the manufactured AFC carried out by Wagner-*Rousett and colleagues established the integrity of the ADC surrogate was not comprised and was well suited for research and development of ADCs without the risk of exposure to cytotoxic agents.* [*mAbs*, 2014. 6(1): p. 173-184.] As part of the conjugation process, reactive maleimide containing valine-citrulline linker that did not undergo conjugation were quenched through the addition N-acetylcysteine (NAc-linker-DSEA, FIG. 1C) and removed via SEC purification. Assessment of residual drug species was carried out using a multidimensional method that couples an online SPE mixed mode anion exchange column (Oasis® MAX, Waters) with a superficially porous high resolution C18 column (Cortecs $C_{18}$, Waters) with in-line detection performed simultaneously using a tunable UV (ACQUITY TUV, Waters) and single quadrupole MS detector (ACQUITY QDa, Waters).

Reference Standards

Figure 5:
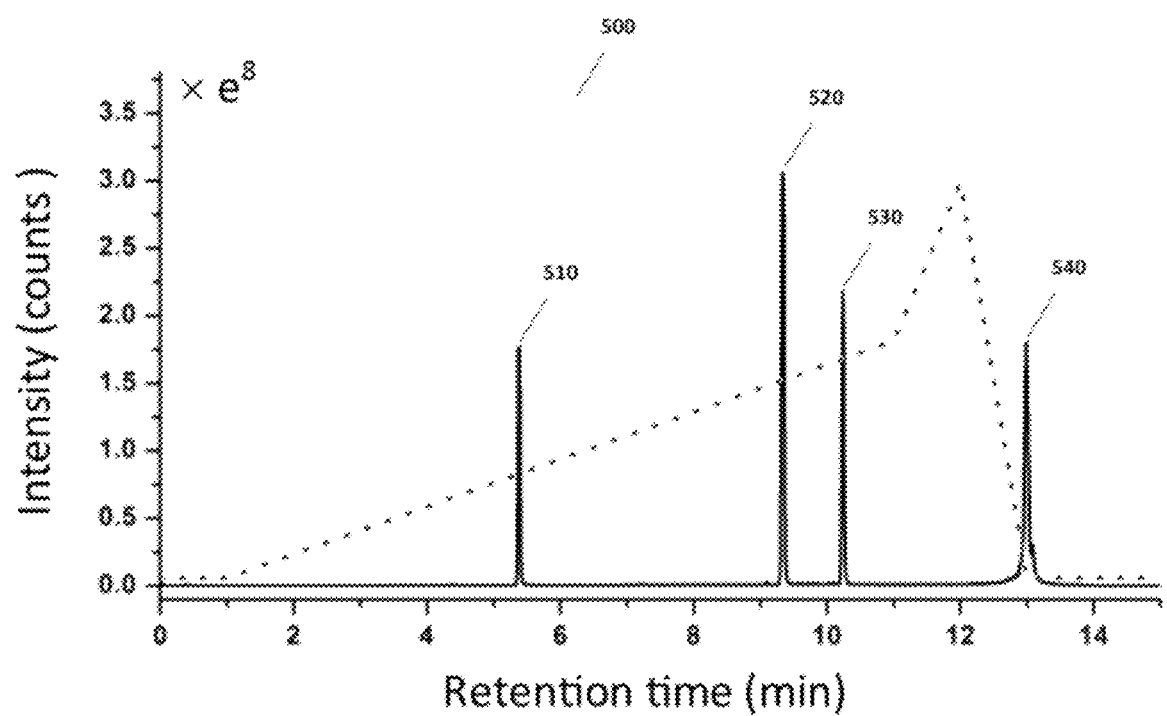
FIG. 5 shows the reference standard evaluation using a mixture of the three reference standards, which were base line resolved within the applied gradient (500). DSEA (510), NAc-linker-DSEA (520), and Mal-linker-DSEA (530) reference standards were separated over a 10 min gradient from 5%-50% (dashed line) with acetonitrile, 0.1% FA v/v, as the organic mobile phase using a superficially porous C18 RPLC column. 540 represents the conditioning peak. Combined spectrum from SIRs collected using the $[M+H]^{+1}$ and $[M+2H]^{+2}$ charge state for each component using optimized MS settings (see "Materials and Methods," found in the Exemplification) is shown.

Reference standards comprised of DSEA, linker-DSEA, and NAc-linker-DSEA were characterized using an ACQUITY H-Class Bio with 2D technology (Waters Corp.) in 1DLC configuration (see "Materials and Methods"). A 10 min reversed phase (RP) gradient was performed using a superficially porous 2.1×50 mm, 2.7 um C18 column (Cortecs $C_{18}$, Waters) to assess the suitability of the reference standards for the proposed method. Selected ion recording (SIR) of the [M+1H]+1 and [M+2H]+2 charge state were collected for each standard. As shown in FIG. 5, a mixture of the three reference standards were base line resolved within the applied gradient (500). Interestingly, the DSEA (510) drug mimic was notably less hydrophobic than the mal-linker-DSEA (530) and NAc-linker-DSEA (520) standards eluting at 24% organic mobile phase (MP) composition compared to 42% and 46% MP composition for the NAc-linker-DSEA and mal-linker-DSEA standards, respectively. Relative retention times of the NAc-linker-DSEA and mal-linker-DSEA were similar to RPLC results observed by Li et al [*J Chromatogr A*, 2015. 1393: p. 81-8] using the same valine-citrulline linker. The free drug mimic (DSEA) was less hydrophobic in comparison.

Reference Standard Calibration Plot

Serial dilutions of the mal-linker-DSEA and NAc-linker-DSEA standards were analyzed in triplicate using a 10 min RP gradient with the same instrument and column configuration as FIG. 5. Data acquisition was performed simultaneously using a tunable UV detector set at a absorbance wavelength of 280 nm and a single quadrupole MS detector using SIRs of the [M+2H]+2 charge state for each standard. Acquired data was integrated, plotted, and analyzed using regression analysis for the SIR (FIG. 6) and TUV chromatograms (data not shown). Assay suitability was evaluated using regulatory guidelines [Green, J. M. *Analytical Chemistry*, 1996. 68(9): p. 305A-309A] for precision (<20% R. S. D. at the LOQ, otherwise <15%) and accuracy (<20% relative error (R. E.) at the LOQ, otherwise <15%) to determine the dynamic range of the method.

An ordinary linear regression was determined to model the data accurately. The dynamic range (Table 1) for the single quadrupole was determined to span 2.5 orders of magnitude (0.27 ng/mL-137.70 ng/mL) for the mal-linker-DSEA standard and 2.5 orders of magnitude (0.33 ng/mL-170.90 ng/mL) for the NAc-linker-DSEA standard with LOQs of 0.27 ng/mL (1.35 pg on-column; SNR D 9.56) and 0.33 ng/mL (1.65 pg on-column; SNR D 9.97), respectively. The dynamic range results combined with the good agreement of fitted data at lower concentrations (FIG. 6, inset), suggests a limit of detection of 0.10 ng/mL (0.5 pg on-column) should be achievable with the proposed assay. In practice, an undesirable level of data processing is required at lower concentrations for proper integration, preventing accurate analysis. Nonetheless, the ability to detect target compounds at a nominal 0.3 ng/mL (1.5 pg on-column) demonstrates the methods ability to detect drug compounds with a high degree of sensitivity.

The linear dynamic range of the TUV measurement (Table 1) was determined to span 2 order of magnitude formal-linker-DSEA (34.42 ng/mL-4,406.25 ng/mL) and NAc-linker-DSEA (85.45 ng/mL-5,468.75 ng/mL) standard with the LOQ determined to be 34 ng/mL (0.17 ng on-column) and 85 ng/mL (0.43 ng on-column), respectively. The UV measurement was not evaluated at higher concentrations to extend the dynamic range as higher concentrations would be outside current regulatory recommendations for allowable impurity levels. The lower sensitivity (or the higher detection limit) of the TUV measurement was not unexpected, and supports the investigation to configure in-line MS detection for improved sensitivity. Incorporation of mass detection extended the sensitivity of the proposed method 2 orders of magnitude beyond traditional UV-based detection and was 150-fold more sensitive with an LOQ of 0.30 ng/mL (1.5 pg on-column) for free-drug species compared to previously published methods that used a SEC-RPLC/UV configuration for a similar compound. [Li Y et al. *J Chromatogr A* 2015; 1393:81-8.]

Solid Phase Extraction Optimization

Method development for the multidimensional approach was performed independently for each dimension prior to coupling columns for AFC analysis as an efficient means to perform diagnostic runs. Optimization of an SPE method using a 2.1×20 mm, 30 um SPE column (Oasis MAX, Waters) was performed to evaluate the elution window required to transfer the mal-linker-DSEA and NAc-linker-DSEA from the $1^{st}$ dimension (SPE column) to the $2^{nd}$ dimension (analytical C18 column). For this purpose, the 2D LC configuration shown in FIGS. 4A-C was used with a stainless steel union in lieu of the $2^{nd}$ dimension column with the left and right valve set in position 2.

Table 2 shows the column manager event table. Extracted drug species were transferred in a 5.50 elution window using at-column-dilution with both valves in position 2 to refocus eluting drug species at the head of the analytical column. The transfer was bracketed with a 0.6 second interval in position 2,1 to purge the fluidic path.

TABLE 1

Assay suitability. Analyses of standards were performed in triplicate and evaluated using ICH guidelines for precision (<20% R.SD at the LOQ, otherwise <15%) and accuracy (<20% relative error (R.E.) at the LOQ, otherwise <15%). The dynamic range was extended 2 orders of magnitude using the quadrupole MS detector in a serial configuration with the LC-TUV optical detector.

| | N = 3 | | TUV | | | MS | | |
|---|---|---|---|---|---|---|---|---|
| Ref. Sample | Conc. (ng/ml) | Mass load (pg) | Area | R.SD (%) | R.E. (%) | Area | R.SD (%) | R.E. (%) |
| | | | Mal-Linker-DSEA | | | | | |
| 1 | 4406.25 | 22031.25 | 196.67 | 2.35 | 99.80 | 1195858 | 18.32 | 78.08 |
| 2 | 2203.13 | 11015.65 | 99.35 | 2.13 | 100.55 | 667774 | 11.20 | 87.20 |
| 3 | 1101.56 | 5507.80 | 50.05 | 1.80 | 100.74 | 358237 | 9.78 | 93.55 |
| 4 | 550.78 | 2753.90 | 25.53 | 1.75 | 101.66 | 184526 | 8.42 | 96.37 |
| 5 | 275.39 | 1376.95 | 12.80 | 3.56 | 99.71 | 94516 | 7.52 | 98.71 |
| 6 | 137.70 | 688.50 | 6.64 | 4.04 | 99.25 | 47794 | 6.48 | 99.80 |
| 7 | 68.85 | 344.25 | 3.20 | 2.14 | 88.35 | 24108 | 4.49 | 100.62 |
| 8 | 34.42 | 172.10 | 1.67 | 2.73 | 80.16 | 12057 | 3.17 | 100.53 |
| 9 | 17.21 | 86.05 | | | | 6089 | 4.47 | 101.29 |
| 10 | 8.61 | 43.05 | | | | 2992 | 4.00 | 99.08 |
| 11 | 4.30 | 21.50 | | | | 1476 | 2.95 | 96.89 |
| 12 | 2.15 | 10.75 | | | | 728 | 6.81 | 93.75 |
| 13 | 1.08 | 5.40 | | | | 373 | 0.61 | 92.79 |
| 14 | 0.54 | 2.70 | | | | 191 | 2.61 | 88.67 |
| 15 | 0.27 | 1.35 | | | | 103 | 2.74 | 85.11 |
| | | | NAc-Linker-DSEA | | | | | |
| 1 | 5468.75 | 27343.75 | 262.41 | 1.23 | 100.17 | 1081872 | 18.77 | 81.78 |
| 2 | 2734.35 | 13671.90 | 131.17 | 2.07 | 99.31 | 591076 | 14.83 | 89.35 |
| 3 | 1367.19 | 6835.95 | 66.52 | 2.35 | 99.08 | 311053 | 10.56 | 94.05 |
| 4 | 683.59 | 3417.95 | 35.87 | 3.50 | 103.49 | 161949 | 6.75 | 97.93 |
| 5 | 341.80 | 1709.00 | 18.59 | 4.21 | 100.90 | 82233 | 4.81 | 99.44 |
| 6 | 170.90 | 854.50 | 10.66 | 2.06 | 103.42 | 41406 | 3.66 | 100.13 |
| 7 | 85.45 | 427.25 | 5.61 | 2.62 | 89.68 | 20543 | 2.41 | 99.32 |
| 8 | 42.72 | 213.60 | | | | 10409 | 2.77 | 100.60 |
| 9 | 21.36 | 106.80 | | | | 5178 | 2.99 | 99.96 |
| 10 | 10.68 | 53.40 | | | | 2646 | 2.15 | 101.93 |
| 11 | 5.34 | 26.70 | | | | 1311 | 6.12 | 100.54 |
| 12 | 2.67 | 13.35 | | | | 625 | 3.28 | 94.91 |
| 13 | 1.34 | 6.70 | | | | 322 | 4.18 | 95.89 |
| 14 | 0.67 | 3.35 | | | | 190 | 2.45 | 109.53 |
| 15 | 0.33 | 1.65 | | | | 95 | 5.33 | 102.17 |

TABLE 2

Column manager event table for the instrument of FIGS. 4A-C.
Column manager: event table

| Time (min) | Event | Action |
|---|---|---|
| Initial | Left Valve | Position 1 |
| initial | Right Valve | Position 1 |
| 12.00 | Left Valve | Position 2 |
| 12.01 | Right Valve | Position 2 |
| 17.50 | Right Valve | Position 1 |
| 17.51 | Left Valve | Position 1 |

A small aliquot of the dilute trastuzumab sample used for column conditioning was spiked with mal-linker-DSEA and NAc-linker-DSEA reference standards. The spiked trastuzumab sample was injected onto the SPE column with screening conditions based on RPLC results of the reference standards. The initial and eluting MP composition was adjusted in an iterative fashion until no observable ions related to the reference standards were detected between the 5 min to 12 min and 15 min to 20 min portion of the MS chromatogram. Presence of ions between 5-12 min would indicate poor retention of reference standards, while ions detected between 15-20 min would indicate poor recovery of the reference standards. The optimized composition was determined to be 18% and 36% organic solvent for the loading and elution conditions, respectively.

Figure 8:
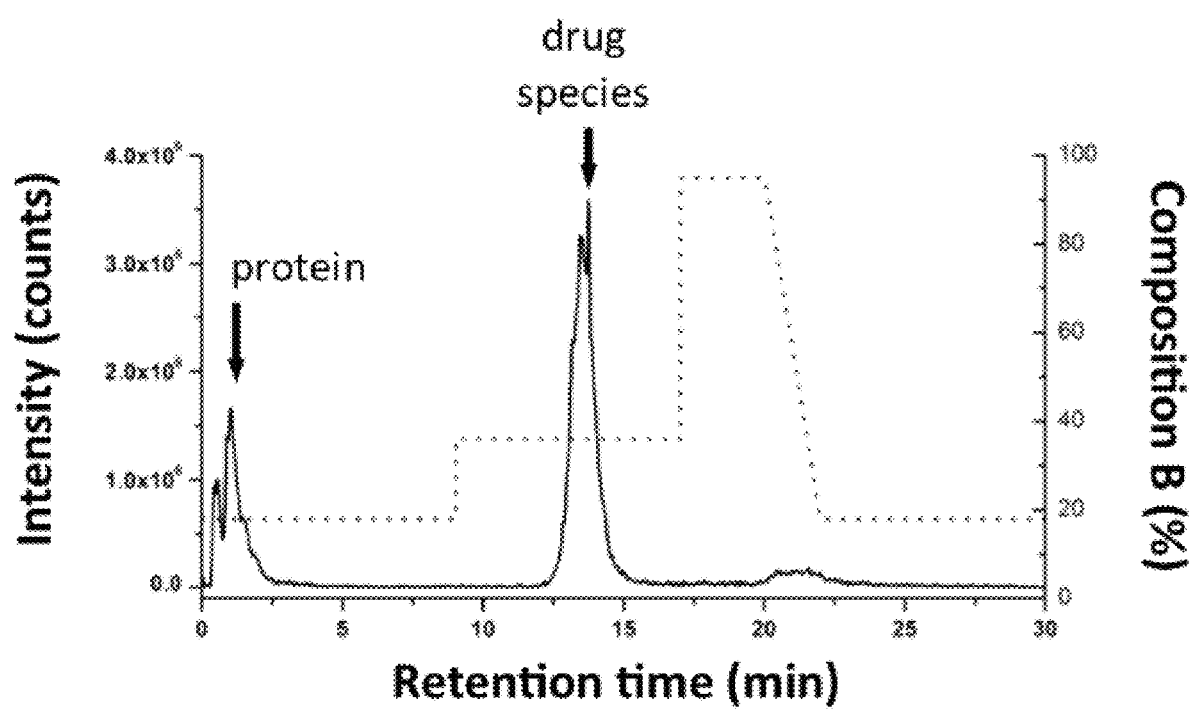
FIG. 8 depicts the method evaluation of SPE with spiked sample. DSEA, mal-linker-DSEA, and NAc-linker-DSEA was spiked into a neat AFC sample for SPE optimization. Optimal SPE loading conditions for the extraction of mal-linker-DSEA and NAc-linker-DSEA components from the spiked AFC sample were determined to be 18% acetonitrile, 2% FA. A step gradient to 36% acetonitrile, 2% FA was determined to be optimal conditions to elute bound drug components in a narrow peak centered around 13.5 min.

As shown in FIG. 8, using these conditions allows the protein to be passed to waste with the retained reference standards eluting in a relatively narrow window using a minimum amount of organic MP for improved at-column-dilution efficiency.

Figures 9A, 9B:
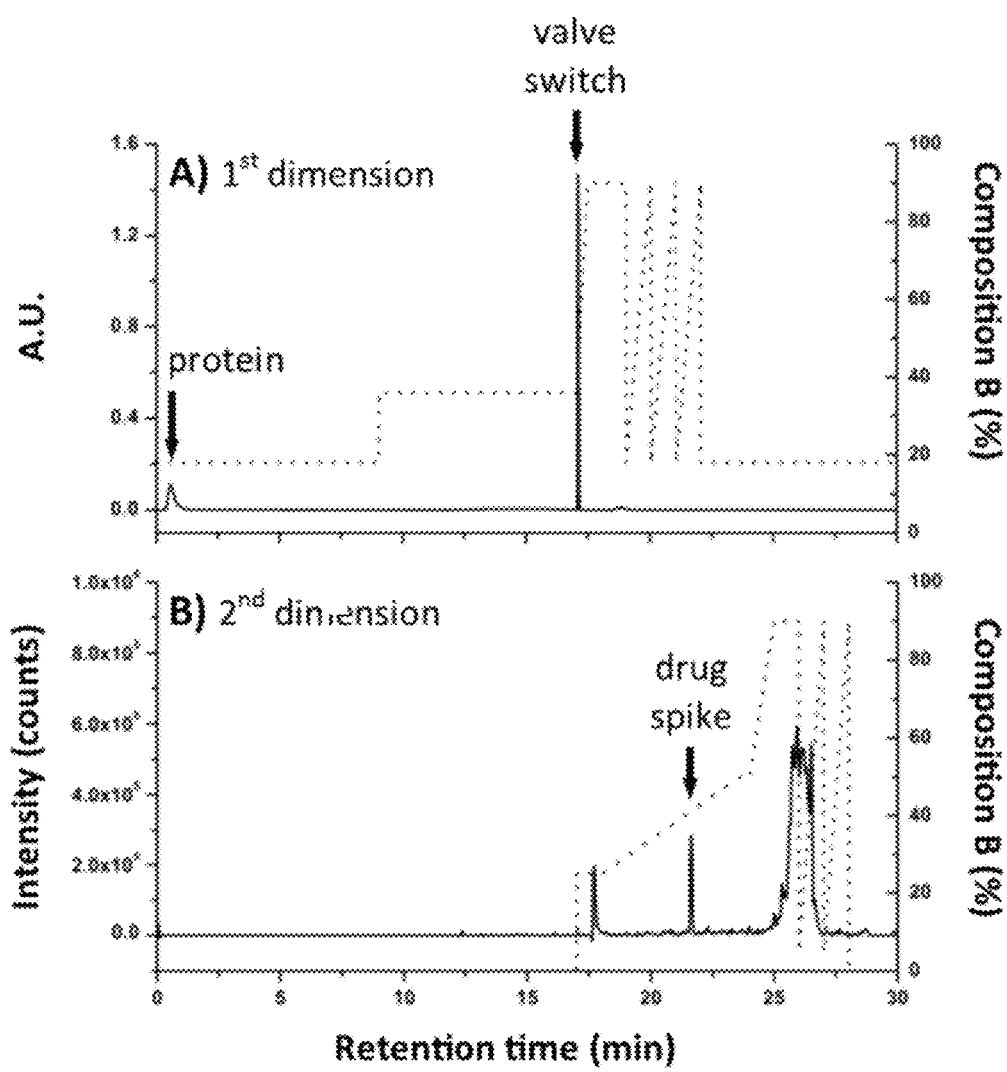
FIGS. 9A-B depict the evaluation of 2DLC configuration. NAc-linker-DSEA, spiked into an AFC sample, was successfully transferred from A) SPE ($1^{st}$ dimension) to the B) RPLC ($2^{nd}$ dimension) using the 2DLC configuration illustrated in FIGS. 4A-B as proof-of-principle.

To verify, the stainless steel union was replaced with the $2^{nd}$ dimension superficially porous $C_{18}$ RP column and initial valve states were set to position 1. A fresh aliquot of the dilute trastuzumab sample was spiked with just the NAc-linker-DSEA reference standard and injected using the optimized conditions as described for the AFC analysis (see "Materials and Methods") with timed valve changes occurring as indicated in Table 1. As shown in FIG. 9A, the protein was eluted in the void upon initial injection allowing the spiked NAc-linker-DSEA to be successfully transferred and re-focused onto the $2^{nd}$ dimension RPLC column with subsequent elution using a 10 minute gradient (FIG. 9B).

Recovery Efficiency Evaluation

With successful transfer of the NAc-linker-DSEA reference standard using the proposed 2DLC configuration, a natural extension is to test the recovery efficiency of the method. Four samples of the NAc-linker-DSEA were prepared at nominal concentrations of 2 ng/mL, 17 ng/mL, 74 ng/mL, 146 ng/mL representing four points spaced throughout the dynamic range of the method as determined by regression analysis of the quadrupole MS data. Injections were performed in triplicate in both 1DLC and 2DLC instrument configurations. Peak area was compared for both instrument configurations to assess recovery. Recovery was determined to be within recommended guidelines [Green, J. M. Analytical Chemistry, 1996. 68(9): p. 305A-309A.] as shown in Table 3, with precision (R. S. D.) below 5% for both configurations and accuracy (R. E.) within 3%. These results indicate the SPE column was efficiently extracting the NAc-linker-DSEA sample from the eluent with no observable loss of standard in the void. In addition, the agreement in area between both 1D and 2D configurations indicate transfer efficiency between columns was maintained with no loss introduced by the stainless steel tee used for at-column-dilution. The combined recovery results indicate the proposed multidimensional method to couple SPE-RPLC is sufficiently robust and fit-for-purpose with recovery of the NAc-linker-DSEA standard demonstrated across the established dynamic range.

TABLE 3

2DLC recovery evaluation. Nac-linker-DSEA reference standard was prepared at four concentrations throughout the experimentally determined dynamic range and evaluate for recovery efficiency using the 2DLC configuration illustrated in FIG. 7. Identical separations were performed in a 1DLC configuration using the same system with a union in lieu of the SPE column ($1^{st}$ dimension) as a reference. Comparison of peak area across triplicate injections of the NAc-linker-DSEA reference standard indicate sample recovery was equivalent between both 1DLC and 2DLC configurations.

| Conc. | 1DLC | | | 2DLC | | |
|---|---|---|---|---|---|---|
| (ng/mL) | Area | R.S.D. (%) | R.E. (%) | Area | R.S.D. (%) | R.E. (%) |
| 2 | 458 | 5.2 | 95.4 | 482 | 1.7 | 100.4 |
| 17 | 4117 | 0.2 | 99.6 | 4146 | 1.0 | 100.3 |
| 74 | 17776 | 1.7 | 99.2 | 18063 | 2.7 | 100.8 |
| 146 | 35556 | 1.9 | 101.0 | 34839 | 0.2 | 99.0 |

AFC Sample Analysis

Figure 6:
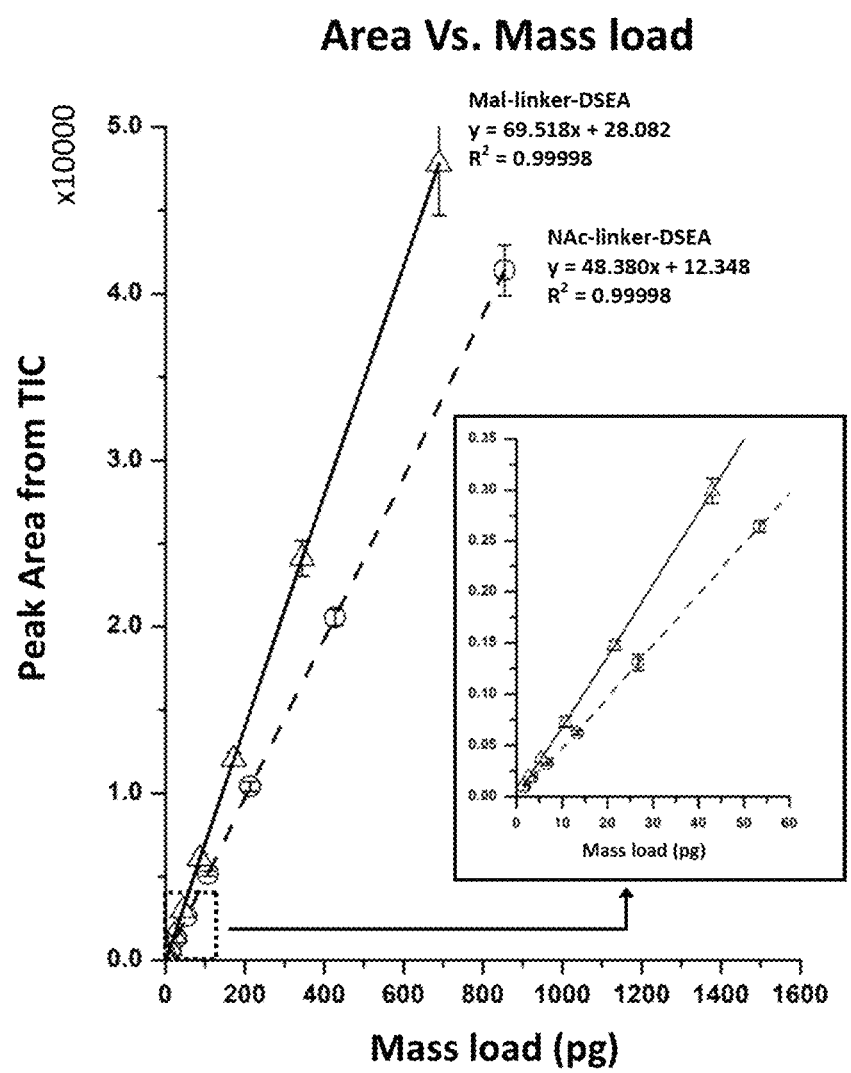
FIG. 6 shows the assay dynamic range. Analysis of reference standards were performed in triplicate. Calibration plots of the reference standards were generated using peak area from SIRs for the most abundant $[M+2H]^{+2}$ charge state and fitted with an ordinary linear regression model. Using ICH guidelines the MS quadrupole dynamic range was determined to be 1.35 pg-688.5 pg for the mal-linker-DSEA and 1.65 pg-854.5 pg for the NAc-Linker-DSEA reference standards.
Figure 7A:
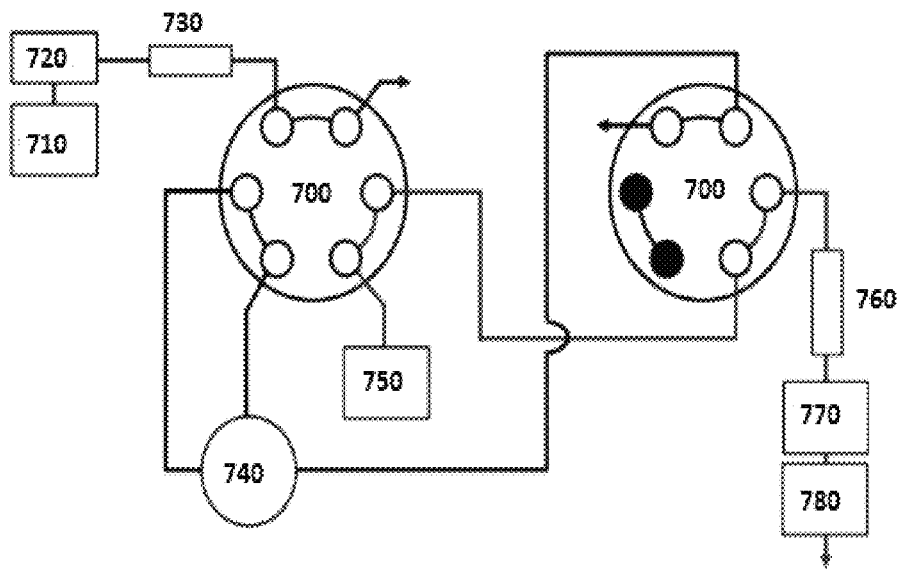
FIGS. 7A-C depict the instrument configuration schematic. A column manager housing two 6-port 2-position valves was configured as illustrated by the schematic to facilitate transfer of retained drug species between the SPE ($1^{st}$) (730) and RPLC ($2^{nd}$) (760) dimensions. Valve position is denoted numerically as position 700 and 705. The other components of the instrument include: QSM: quaternary solvent manager (710), AS: auto sampler (720), ACD: at-column dilution (740); TUV: tunable ultraviolet detector (770), BSM: binary solvent manager (750), MS: mass spectrometer (780).
Figure 7B:
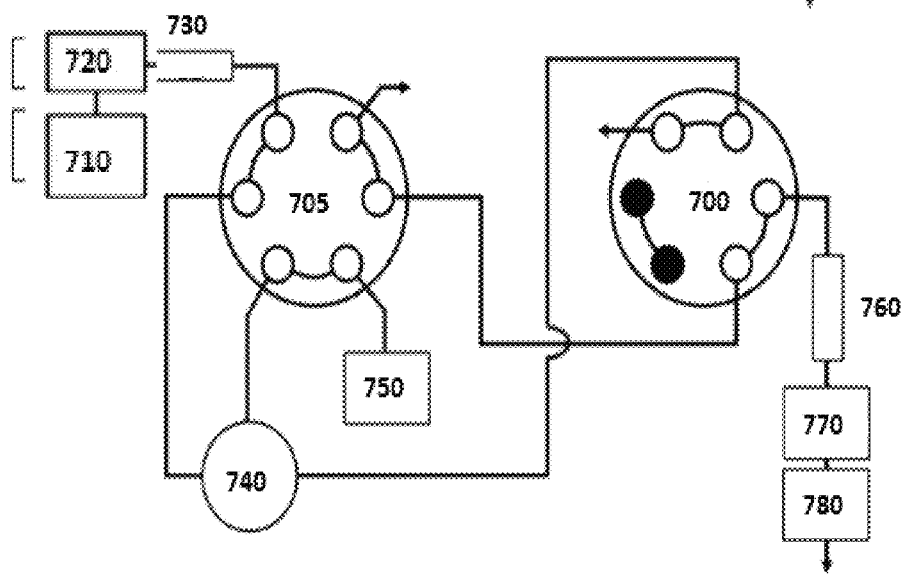
Figure 7C:
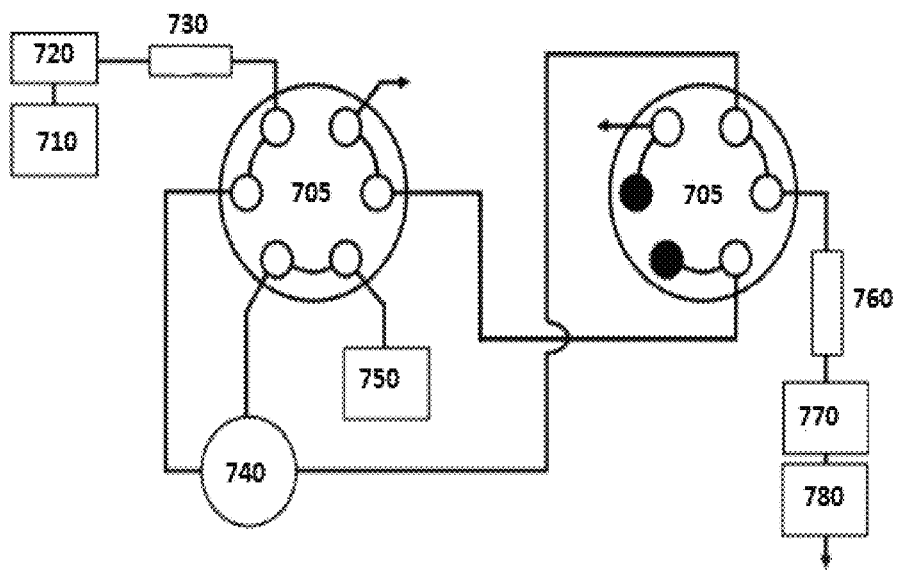

AFC samples were used as received at a concentration of (1.94 mg/mL) without additional preparation and were evaluated for the presence of mal-linker-DSEA and NAc-linker-DSEA using the 2DLC configuration shown in FIG. 7. A 10 µL injection of neat AFC sample was analyzed in triplicate using the same method as before (see "Materials and Methods"). The same separation was performed using a water blank prior to each sample run to assess carry-over. As shown in FIG. 10A, triplicate SIR spectrum overlays of the blank injections show no observable carry-over of the NAc-linker-DSEA species at 22 min and negligible carry-over (<5% by area) of the mal-linker-DSEA species eluting at 23 min indicating the method is reproducible and can be performed over multiple runs for extended column use. The presence of NAc-linker-DSEA and mal-linker-DSEA in the AFC sample was confirmed as shown in FIG. 10B with both species eluting reproducibly at 22 min and 23 min, respectively. Method precision was confirmed upon closer examination of the data as shown in Table 4, with R. S. D. determined to be less than 3% for both the mal-linker-DSEA and NAc-linker-DSEA drug components. Using the MS based calibration plot (FIG. 6), the concentration of the free-drug components were determined to be 7.19 ng/mL and 3.82 ng/mL for the NAc-linker-DSEA and mal-linker-DSEA components, respectively. Detection of drug species at these levels, in a sample of modest concentration and injection volume, is not possible with optical detection alone, thus accenting the utility of an MS equipped 2DLC method such as this.

TABLE 4

AFC sample results. NAc-linker-DSEA and mal-linker-DSEA were detected within dynamic range of the assay (FIG. 6) as recommended by ICH guidelines. The concentration of NAc-linker-DSEA and mal-linker-DSEA was determined to be 7.19 ng/ml and 3.82 ng/ml, respectively.

| | NAc-Linker-DSEA | | | Mal-Linker-DSEA | | |
| --- | --- | --- | --- | --- | --- | --- |
| Injection | Area | Experimental mass (pg) | Experimental conc. (ng/ml) | Area | Experimental mass (pg) | Experimental conc. (ng/ml) |
| 1 | 3476 | 71.59 | 7.16 | 2716 | 38.67 | 3.87 |
| 2 | 3429 | 70.62 | 7.06 | 2746 | 39.10 | 3.91 |
| 3 | 3563 | 73.39 | 7.34 | 2599 | 36.98 | 3.70 |
| Mean | 3489 | 71.87 | 7.19 | 2687 | 38.25 | 3.82 |
| S.D. | 68 | 1.41 | 0.14 | 78 | 1.12 | 0.11 |
| R.S.D. | 1.95 | 1.96 | 1.96 | 2.89 | 2.92 | 2.92 |

Discussion

Traditional methods for the detection, characterization, and quantification of trace free drug species have included assays based on ELISA and RPLC techniques with varying success. [Stephan, J. P., K. R. Kozak, and W. L. Wong *Bioanalysis*, 2011. 3(6): p. 677-700; Kozak, K. R., et al. *Bioconjug Chem*, 2013. 24(5): p. 772-9.] The reduction of sample preparation steps through the incorporation of multidimensional techniques has afforded analysts more efficient methods for assessment of trace drug species with improved sensitivity. Selection of orthogonal column chemistries for multi-dimensional assays can be a challenging prospect as eluents and format can impact assay specificity, efficiency, and sensitivity. [Fleming, M. S., et al., *Analytical Biochemistry*, 2005. 340(2): p. 272-278; Li, Y., et al., *J Chromatogr A*, 2015. 1393: p. 81-8; He, Y., et al. *J Chromatogr A*, 2012. 1262: p. 122-9.] The targeted removal of APIs from biological matrices using SPE based techniques has been well established in the pharmaceutical industry. To that end, SPE techniques are becoming more prevalent in the characterization and routine testing of biopharmaceuticals. [Souverain, S., S. Rudaz, and J. L. Veuthey, *Journal of Chromatography B*, 2004. 801(2): p. 141-156.] Method flexibility with off-line and on-line options combined with the ability to use volatile solvents makes SPE techniques ideal for multidimensional approaches with MS detection. The unique mixed mode OASIS chemistry facilitates the ability to separate complex mixtures based on different physicochemical properties and are ideal when considering the unique nature of ADCs which are comprised of hydrophilic substrates conjugated to hydrophobic drugs. [Wakankar, A., et al. *mAbs*, 2011. 3(2): p. 161-172.] The current study has addressed challenges associated with residual free drug analysis through the development of a MS compatible multidimensional approach that couples SPE-RPLC chemistries that is specific and sensitive.

Targeting free or non-conjugated hydrophobic drug species for selective extraction is achieved through the use of a hydrophobic SPE resin interspersed with anion exchange functional groups. Conceptually, net positive substrates such as mAbs in solution at pH below their pI are passed through the positively charged SPE material including mAb species with attached drug. In contrast, free drug and associated products are adsorbed to the mixed mode surface of the SPE ligand for downstream analysis. The current study successfully demonstrated this approach through the capture and elution of a clinically relevant valine-citrulline based surrogate molecule and its N-acetyl-cysteine quenched product from an unadulterated ADC mimic sample using an SPE-RPLC/MS approach. Similar hydrophobic characteristics observed in the surrogate molecules with established literature supports the viability of this method in clinical practice. [Li, Y., et al. *J Chromatogr A*, 2015. 1393: p. 81-8.]

The success of the proposed method relies on several key aspects working in a synergistic manner. The implementation of a SPE column as the $1^{st}$ dimension, which is retentive towards API species, facilitates a means for analysts to tune the specificity of the method for varying substrates or drug candidates. In contrast, $1^{st}$ dimension separations such as SEC do not provide the same degree of specificity or selectivity. In addition, the mixed mode SPE column efficiently removes protein substrates due to like charge repulsion and reduces carry-over allowing for repeated column use. As the trapped drug species are very hydrophobic, they are eluted at an organic percent which could reduce the $2^{nd}$ dimension RP chromatography performance. To overcome this challenge, at-column-dilution was incorporated to efficiently retain drug products in the Pt dimension eluent at the head of the $2^{nd}$ dimension column. [Hurwitz E Fau—Levy, R., et al. *Cancer Research*, 1975. 35: p. 1175-1181; Souverain, S., S. Rudaz, and J. L. Veuthey *Journal of Chromatography* B, 2004. 801(2): p. 141-156.] The degree to which the eluent needs to be diluted will depend on the organic strength necessary to elute drug products from the $1^{st}$ dimension, but is easily adjusted using the proposed configuration. The improved $2^{nd}$ dimension separation efficiency afforded by the inclusion of at-column-dilution, combined with in-line MS detection, increased the sensitivity of the assay 125-fold for the mal-linker-DSEA and 250-fold for the NAc-linker-DSEA drug species with a nominal LOQ of 0.3 ng/mL when compared to UV detection (Table 4).

The current studies MS based method represents over a 150-fold improvement in sensitivity compared to the SEC-RPLC/UV method described by Li et al. using similar, but not identical drug species. [Li, Y., et al. *J Chromatogr A*, 2015. 1393: p. 81-8.] In addition to improved sensitivity, the ability to efficiently recover trace levels of drug species across a wide dynamic range makes the proposed method ideal for assessment of free drug species throughout a ADCs product life cycle including development, formulation, and clinical trials.

sensitive for free drug analysis. Future work will include evaluation of the proposed method for extraction of free drug species using a diverse panel of clinically relevant ADCs in formulation and biological matrices.

TABLE 4

Assay suitability. Analyses of standards were performed in triplicate and evaluated using ICH guidelines for precision (<20% R.S.D. at the LOQ, otherwise <15%) and accuracy (<20% relative error (R.E.) at the LOQ, otherwise <15%). The dynamic range (gray highlight) was extended 2 orders of magnitude using the quadrupole MS detector in a serial configuration with the LC-TUV optical detector.

| N = 3 | | | TUV | | | MS | | |
|---|---|---|---|---|---|---|---|---|
| Ref. Sample | Conc. (ng/ml) | Mass load (pg) | Area | R.S.D. (%) | R.E. (%) | Area | R.S.D. (%) | R.E. (%) |
| Mal-Linker-DSEA | | | | | | | | |
| 1 | 4406.25 | 22031.25 | 196.67 | 2.35 | 99.80 | 1195858 | 18.32 | 78.08 |
| 2 | 2203.13 | 11015.65 | 99.35 | 2.13 | 100.55 | 667774 | 11.20 | 87.20 |
| 3 | 1101.56 | 5507.80 | 50.05 | 1.80 | 100.74 | 358237 | 9.78 | 93.55 |
| 4 | 550.78 | 2753.90 | 25.53 | 1.75 | 101.66 | 184526 | 8.42 | 96.37 |
| 5 | 275.39 | 1376.95 | 12.80 | 3.56 | 99.71 | 94516 | 7.52 | 98.71 |
| 6 | 137.70 | 688.50 | 6.64 | 4.04 | 99.25 | 47794 | 6.48 | 99.80 |
| 7 | 68.85 | 344.25 | 3.20 | 2.14 | 88.35 | 24108 | 4.49 | 100.62 |
| 8 | 34.42 | 172.10 | 1.67 | 2.73 | 80.16 | 12057 | 3.17 | 100.53 |
| 9 | 17.21 | 86.05 | | | | 6089 | 4.47 | 101.29 |
| 10 | 8.61 | 43.05 | | | | 2992 | 4.00 | 99.08 |
| 11 | 4.30 | 21.50 | | | | 1476 | 2.95 | 96.89 |
| 12 | 2.15 | 10.75 | | | | 728 | 6.81 | 93.78 |
| 13 | 1.08 | 5.40 | | | | 373 | 0.61 | 92.79 |
| 14 | 0.54 | 2.70 | | | | 191 | 2.61 | 88.67 |
| 15 | 0.27 | 1.35 | | | | 103 | 2.74 | 85.11 |
| NAc-Linker-DSEA | | | | | | | | |
| 1 | 5468.75 | 27343.75 | 262.41 | 1.23 | 100.17 | 1081872 | 18.77 | 81.78 |
| 2 | 2734.38 | 13671.90 | 131.17 | 2.07 | 99.31 | 591076 | 14.83 | 89.36 |
| 3 | 1367.19 | 6835.95 | 66.52 | 2.35 | 99.08 | 311053 | 10.56 | 94.05 |
| 4 | 683.59 | 3417.95 | 35.87 | 3.50 | 103.49 | 161949 | 6.75 | 97.93 |
| 5 | 341.80 | 1709.00 | 18.59 | 4.21 | 100.90 | 82233 | 4.81 | 99.44 |
| 6 | 170.90 | 854.50 | 10.66 | 2.06 | 103.42 | 41406 | 3.66 | 100.13 |
| 7 | 85.45 | 427.25 | 5.61 | 2.62 | 89.68 | 20543 | 2.41 | 99.32 |
| 8 | 42.72 | 213.60 | | | | 10409 | 2.77 | 100.60 |
| 9 | 21.36 | 106.80 | | | | 5178 | 2.99 | 99.96 |
| 10 | 10.68 | 53.40 | | | | 2646 | 2.15 | 101.93 |
| 11 | 5.34 | 26.70 | | | | 1311 | 6.12 | 100.54 |
| 12 | 2.67 | 13.35 | | | | 625 | 3.28 | 94.91 |
| 13 | 1.34 | 6.70 | | | | 322 | 4.18 | 95.89 |
| 14 | 0.67 | 3.35 | | | | 190 | 2.45 | 109.53 |
| 15 | 0.33 | 1.65 | | | | 95 | 5.33 | 102.17 |

As potentially more potent drug candidates for ADCs are identified [Thorson, J. S., et al. *Current Pharmaceutical Design*, 2000. 6(18): p. 1841-1879; Clardy, J. and C. Walsh *Nature*, 2004. 432(7019): p. 829-837], efforts to expand the therapeutic window will require assays with improved sensitivity for the assessment and characterization of residual free drug species to ensure product safety and efficacy. [Wakankar, A., et al. *mAbs*, 2011. 3(2): p. 161-172.] The utility of multidimensional approaches in the characterization of biopharmaceuticals is becoming increasingly evident [Fleming, M. S., et al. *Analytical* Biochemistry, 2005. 340 (2): p. 272-278; Li, Y., et al. *J Chromatogr A*, 2015. 1393: p. 81-8; He, Y., et al. *J Chromatogr A*, 2012. 1262: p. 122-9; Li, Y., et al. *Analytical Chemistry*, 2014. 86(10): p. 5150-5157; Stoll, D. R., et al. *Analytical Chemistry*, 2015. 87(16): p. 8307-8315; Zhang, K., et al. *Journal of Separation Science*, 2013. 36(18): p. 2986-2992.]. In this study the SPE-RPLC/MS multidimensional approach combined with at-column-dilution was demonstrated as an efficient means to bypass lengthy sample preparation steps while enabling control over each dimension; promoting a method that can be readily adapted to existing workflows that is specific and Material and Methods Chemicals and reagents were purchased from Sigma Aldrich unless otherwise stated. Mass spectrometry grade solvents were used for mobile phase and sample preparation.

Antibody and Linker-Payload Production and Purification

This AFC is based on the conjugation of dansyl sulfonamide ethyl amine (DSEAEA)-linker maleimide on interchain cysteines of trastuzumab used as a reference antibody. The trastuzumab used in this study is the European Medicines Agency-approved version and formulation (21 mg/mL). The linker-fluorophore payload was designed to mimic the linker-drug most frequently used in ADC clinical trials. The synthesis was briefly reported in the supplemental material by Wagner-Rousset et al. [46] It consists of maleimide-caproic acid dansyl sulfonamide ethyl amine (mc_D-SEA, structure FIG. 1A) with a valine-citruline linker that mimics the cytotoxic agent and linker conjugated to mAbs through reduced interchain cysteine via the maleimide function.

Mild reduction of trastuzumab and coupling of DSEA-linker were performed as previously described. [Sun, M. M., et al. *Bioconjug Chem*, 2005. 16(5): p. 1282-90.] Briefly, trastuzumab was reduced with 2.75 equivalents of TCI P in 10 mM borate pH 8.4 buffer containing 150 mM NaCl and 2 mM EDTA for 2 h at 37° C. The concentration of free thiols was determined by using the Ellman's reagent with L-cysteine as standard, typically resulting in around 5 thiols per antibody. To target a DAR of 4, the partially reduced trastuzumab was then alkylated with 2 equivalents of DSEA-linker per thiol in the same buffer for 1 h at room temperature. N-acetyl-cysteine (1.5 equivalents/DSEA-linker) was used to quench any unreacted DSEA-linker. The AFC was purified by size exclusion chromatography on a Superdex 200 pg column (GE Life Sciences) eluted with 25 mM histidine pH 6.5 buffer containing 150 mM NaCl, by using an AKTA Avant biochromatography system (GE Life Sciences). The AFC (average DAR=4.0) was characterized by most of the methods used for hinge-Cys ADCs (nr/rSDS-PAGE, SEC, HIC, Native MS, LC-MS (IdeS/Red) and yielded similar profiles as those reported for brentuximab vedotin. [Wagner-Rousset, E., et al. *mAbs*, 2014. 6(1): p. 173-184; Debaene, F., et al. *Analytical Chemistry*, 2014. 86(21): p. 10674-10683.] Prepared AFC samples were used neat at a concentration of 1.94 mg/mL.

Chromatography

An ACQUITY H-Class Bio equipped with a commercially available 2D technology configuration (Waters Corp.) was used for the experiments. FIG. 7A is a schematic of the instrument setup denoting column, pump, and plumbing configuration for 2DLC with at-column-dilution in place for $2^{nd}$ dimension loading. Transfer of retained analytes on the solid phase extraction (SPE) column ($1^{st}$ dimension) was performed through programmed valve events using the column manager control interface (FIG. 7B). Valve switches were staggered with a 0.01 min delay to purge the at-column-dilution fluidic path prior to and after analyte transfer. A tunable UV detector (ACQUITY TUV, Waters Corp.) equipped with a 5-mm titanium flow cell was incorporated post $2^{nd}$ dimension column to evaluate the optical detection limit of the separated analytes. Single wavelength detection was performed at an Amax of 280 nm with a sampling rate of 20 Hz. 1DLC experiments with the appropriate column and mobile phases (MP) present in the $1^{st}$ dimension column position and quaternary solvent manager (QSM) reservoirs, respectively, were performed using the same system by physically interchanging fluidic path connections post column on both dimensions and leaving the $2^{nd}$ dimension Binary solvent manager (BSM) pump in an idle state with both valves in position 1.

Column Conditioning

A 2.1×20 mm, 30 μm SPE column (Oasis® MAX, Waters Corp.) was conditioned prior to sample runs using a dilute sample of trastuzumab (2 mg/mL) prepared in MS grade $H_2O$ with 0.1% FA v/v. Column conditioning was performed with the chromatography system in a 1DLC configuration at a flow rate of 0.300 mL/min with the column temperature set at 30° C. QSM reservoirs were prepared as MP A: $H_2O$, 2% FA v/v, MP B: acetonitrile, 2% FA v/v. A 2 uL injection of the conditioning sample was separated by performing a 10 min gradient from 0% MP B to 95% MP B until baseline line response stabilized. The $2^{nd}$ dimension column was conditioned in a similar fashion. A 2.1×50 mm, 2.7 um superficially porous C18 column (Cortecs $C_{18}$, Waters Corp.) was conditioned prior to actual sample runs using a dilute mixture of the reference standards (0.5 ng/mL) prepared in 50:50 ACN, 0.1% FA v/v: $H_2O$, 0.1% FA v/v. Mobile phases were prepared as MP A: $H_2O$, 0.1% FA v/v, MP B: acetonitrile, 0.1% FA v/v. A 5 uL injection of the diluted reference mixture was separated using a 10 min gradient from 5% MP B to 50% MP B at a flow rate of 0.300 ml/min and a column temperature of 40° C. Injections were repeated until retention time and detector response stabilized for individual species. The system was re-plumbed in a 2DLC configuration for AFC analysis after conditioning of both columns.

Calibration Standards

Stock reference standards (FIG. 4) were dissolved in neat DMSO and prepared at concentrations of 4 μg/mL, 2.82 μg/mL, and 3.5 μg/mL for DSEA, mal-linker-DSEA, and NAc-linker-DSEA, respectively. Stock solutions were vortexed, briefly centrifuged, and divided into 50 uL aliquots and stored in −80° C. prior to use. Individual stock reference solutions were diluted in a 1:5 ratio using 50:50 ACN 0.1% FA v/v: $H_2O$ 0.1% FA v/v to prepare initial calibration standard solutions. Sequential 1:1 serial dilutions were performed with the initial calibration standard solution for mal-linker-DSEA and NAc-linker-DSEA using 50:50 ACN 0.1% FA v/v: $H_2O$ 0.1% FA v/v. reference standards were evaluated using the chromatography system in a 1DLC configuration with the QSM reservoirs prepared as MP A: $H_2O$, 0.1% FA v/v, MP B: acetonitrile, 0.1% FA v/v, MP C: and D: Acetonitrile. A 5.0 uL injection of each standard was loaded onto a 2.1×50 mm, 2.7 um superficially porous C18 column (Cortecs $C_{18}$, Waters) with the MP composition held constant for 1.0 min at 5% MP B at a flow rate of 0.300 ml/min and a column temperature of 40° C. A 10 min gradient from 5% MP B to 50% MP B was used to elute the reference standard. Column reconditioning was performed using a rapid 1.0 min gradient to increase the organic composition to 80% MP B followed by a 1.0 min gradient to initial conditions (5% MP B) and held constant for 2 min.

SPE Optimization

Optimization of the 2.1×20 mm, 30 um SPE column (Oasis® MAX, Waters Corp.) was performed using a small aliquot of the dilute trastuzumab sample spiked with excess mal-linker-DSEA and NAc-linker-DSEA reference standards to increase MS response during acquisition. The LC instrument was configured in the 2DLC configuration shown in FIG. 7 using two 6-port, 2-position valves housed in a column manager (ACQUITY column manager, Waters Corp.). For optimization purposes a stainless steel union was used in place of the $2^{nd}$ dimension column and both valves were set to an initial position of 2. The $1^{st}$ dimension QSM reservoirs were prepared as MP A: $H_2O$, 2% FA v/v, MP B: acetonitrile, 2% FA v/v, MP C: and D: Acetonitrile. The $2^{nd}$ dimension BSM reservoirs were prepared as MP A: $H_2O$, 0.1% FA v/v, MP B: acetonitrile, 0.1% FA v/v. The $2^{nd}$ dimension BSM was programmed to flow at a rate of 0.300 mL/min with a MP composition of 60% MP B ($2^{nd}$ dimension MP reservoirs) to replicate back pressure on the $1^{st}$ dimension column encountered when both columns are in-line. The spiked trastuzumab sample was injected onto the SPE column at a flow rate of 0.100 ml/min with an initial MP composition of 23% MP B ($1^{st}$ dimension MP reservoirs). The gradient was then stepped up to 54% MP B to elute the retained reference standards. The initial and eluting MP composition was adjusted in an iterative fashion until no observable ions related to the reference standards were detected between the 5 min to 12 min and 15 min to 20 min portion of the MS spectrum. The optimized composition was determined to be 18% MP B for the loading conditions and 36% MP B for the elution conditions. Once optimized, the stainless steel union was replaces with the $2^{nd}$ dimension superficially porous C18 column and initial valve states were set to position 1. Proof-of-principle was performed using a fresh aliquot of the dilute trastuzumab sample spiked with a smaller amount of the NAc-linker-DSEA reference standard and injected using the optimized conditions described in the AFC sample analysis.

AFC Sample Analysis ($1^{st}$ Dimension)

AFC samples were analyzed using an optimized 2-step gradient in the $1^{st}$ dimension. QSM reservoirs were prepared as MP A: $H_2O$ containing 2% FA v/v, MP B: acetonitrile containing 2% FA v/v, MP C: and D: Acetonitrile. Neat AFC samples were injected at a volume of 10.0 uL using isocratic conditions set at 18% MP B at a flow rate of 0.100 ml/min and a column temperature of 30° C. After 9 min the MP composition was stepped up to 36% MP B and held constant for 8 min to elute the bound analyte. Transfer of analytes to the $2^{nd}$ dimension RPLC column was achieved through a programmed valve event where the left and right valves were switched to position 2 between the 12.00 and 17.50 min mark of the gradient to combine the fluidic path of the $1^{st}$ and $2^{nd}$ dimension columns. A sharp 0.50 min gradient was used to increase the MP composition to 90% MP B from 17.0 to 17.5 min and held constant for an additional 2.50 min. A saw tooth gradient from 90% MP B to 18% MP B was cycled 3 times to recondition the Oasis MAX SPE column with the final cycle returning to the initial start conditions.

AFC Sample Analysis ($2^{nd}$ Dimension)

BSM reservoirs were prepared as MP A: $H_2O$ containing 0.1% formic acid v/v, MP B: acetonitrile containing 0.1% formic acid v/v. As part of the 2DLC method the $2^{nd}$ dimension MP composition was set at 0% MP B at the time of injection and held constant until the 17.50 min mark at a flow rate of 0.300 ml/min. At-column-dilution was performed in a 1:4 dilution (0.1 mL/min $1^{st}$ dimension pump: 0.3 mL/min $2^{nd}$ dimension pump) via a stainless steel split (Vicci Valco) while the $1^{st}$ and $2^{nd}$ dimension fluidic paths were combined between 12.00 and 17.50 min of the method. After 17.50 min MP composition was stepped to 25% MP B and held for 1 min. A 5.55 min gradient was performed from 25% MP B to 50% MP B and held constant for an additional 0.44 min. After the separation gradient was performed the MP composition was ramped to 90% MP B in 1 min followed by two 1 min saw tooth gradients from 90% MP B to 5% MP B to recondition the RPLC column with the final cycle returning to the initial start conditions.

Recovery Evaluation

Assessment of recovery efficiency of the SPE column was performed using the NAc-linker-DSEA reference standard. Four samples were prepared at a concentrations of 1.7 ng/mL, 16.2 ng/mL, 71.9 ng/mL, and 144.6 ng/mL in 50:50 ACN 0.1% FA v/v: $H_2O$ 0.1% FA v/v to span the dynamic range based on the NAc-linker-DSEA calibration plot (FIG. 6). Using the 2DLC system configuration for the AFC sample analysis described earlier, Injections were performed in triplicate for four reference standard samples. The system was then re-configured in a 1DLC mode, and the QSM reservoirs were changed to MP A: $H_2O$ containing 0.1% FA v/v, MP B: acetonitrile containing 0.1% FA v/v, MP C: and D: Acetonitrile. The same reference samples were directly injected onto the 2.1×50 mm, 2.7 um superficially porous C18 column with the MP composition held constant for 1.0 min at 5% MP B at a flow rate of 0.300 ml/min and a column temperature of 40° C. A 10 min gradient from 5% MP B to 50% MP B was used to elute the reference standard. Column reconditioning was performed using a rapid 1.0 min gradient to increase the organic composition to 80% MP B followed by a 1.0 min gradient to initial conditions 5% MP B and held constant for 2 min. Recovery efficiency was determined by comparing peak area in both 1DLC and 2DLC system configurations.

MS Settings

A single quadrupole mass spectrometer (ACQUITY QDa, Waters Corp.) was used for MS analysis post TUV detector (FIG. 7). SIRs representing the $[M+1H]^{+1}$ and $[M+2H]^{+2}$ of the DSEA, mal-linker-DSEA, and NAc-linker-DSEA were acquired in positive polarity covering a mass to charge range of 30 to 1,250 m/z. A confirmed fragment of the mal-linker-DSEA (m/z 718.4) was also acquired in addition to the other charge states and used for MS optimization. MS data was collected throughout the separation as defined in the chromatography section with the flow continuously passing through the MS capillary. Adjustable instrument settings were set as follows: capillary voltage 0.8 kV, sample cone 2.0 V, source temperature 400° C. Data from the MS analysis were processed within the chromatography data system MassLynx. Respective SIRs for the DSEA, mal-linker-DSEA, and NAc-linker-DSEA samples were summed and a mean smoothed applied with a window size of 5 scans and 1 iteration, followed by integration.

Further embodiments of the present invention may be found as disclosed in Birdsall et al. *mAbs*, 2016. 8(2): 305-317, incorporated herein by reference.

BIBLIOGRAPHY

1. Strebhardt, K. and A. Ullrich, Paul Ehrlich's magic bullet concept: 100 years of progress. *Nat Rev Cancer,* 2008. 8(6): p. 473-480.
2. Wu, A. M. and P. D. Senter, Arming antibodies: prospects and challenges for immunoconjugates. *Nat Biotech,* 2005. 23(9): p. 1137-1146.
3. Reichert, J. M., et al., Monoclonal antibody successes in the clinic. *Nat Biotech,* 2005. 23(9): p. 1073-1078.
4. Doronina, S. O., et al., Development of potent monoclonal antibody auristatin conjugates for cancer therapy. *Nat Biotech,* 2003. 21(7): p. 778-784.
5. Remillard, S., et al., Antimitotic activity of the potent tumor inhibitor maytansine. *Science,* 1975. 189(4207): p. 1002-1005.
6. Junutula, J. R., et al., Site-specific conjugation of a cytotoxic drug to an antibody improves the therapeutic index. *Nat Biotech,* 2008. 26(8): p. 925-932.
7. McDonagh, C. F., et al., Engineered antibody-drug conjugates with defined sites and stoichiometries of drug attachment. *Protein Eng Des Sel,* 2006. 19(7): p. 299-307.
8. Hofer, T., et al., Molecularly Defined Antibody Conjugation through a Selenocysteine Interface. *Biochemistry,* 2009. 48(50): p. 12047-12057.

9. Axup, J. Y., et al., Synthesis of site-specific antibody-drug conjugates using unnatural amino acids. *Proceedings of the National Academy of Sciences*, 2012. 109(40): p. 16101-16106.
10. Sun, M. M., et al., Reduction-alkylation strategies for the modification of specific monoclonal antibody disulfides. *Bioconjug Chem*, 2005. 16(5): p. 1282-90.
11. Pro, B., et al., Brentuximab Vedotin (SGN-35) in Patients With Relapsed or Refractory Systemic Anaplastic Large-Cell Lymphoma: Results of a Phase II Study. *Journal of Clinical Onocology*, 2012. 30(18): p. 2190-2196.
12. Lewis Phillips, G. D., et al., Targeting HER2-positive breast cancer with trastuzumab-DM1, an antibody-cytotoxic drug conjugate. *Cancer Res*, 2008. 68(22): p. 9280-90.
13. Chari, R. V., Targeted cancer therapy: conferring specificity to cytotoxic drugs. *Acc Chem Res*, 2008. 41(1): p. 98-107.
14. Dosio, F., P. Brusa, and L. Cattel, Immunotoxins and Anticancer Drug Conjugate Assemblies: The Role of the Linkage between Components. *Toxins*, 2011. 3(7): p. 848-883.
15. Sanderson, R. J., et al., In vivo drug-linker stability of an anti-CD30 dipeptide-linked auristatin immunoconjugate. *Clin Cancer Res*, 2005. 11(2 Pt 1): p. 843-52.
16. Shen, B.-Q., et al., Conjugation site modulates the in vivo stability and therapeutic activity of antibody-drug conjugates. *Nat Biotech*, 2012. 30(2): p. 184-189.
17. Kovtun, Y. V., et al., Antibody-Drug Conjugates Designed to Eradicate Tumors with Homogeneous and Heterogeneous Expression of the Target Antigen. *Cancer Research*, 2006. 66(6): p. 3214-3221.
18. Stephan, J. P., K. R. Kozak, and W. L. Wong, Challenges in developing bioanalytical assays for characterization of antibody-drug conjugates. *Bioanalysis*, 2011. 3(6): p. 677-700.
19. Li, Y., et al., Limiting degradation of reactive antibody drug conjugate intermediates in HPLC method development. *Journal of Pharmaceutical and Biomedical Analysis*, 2014. 92: p. 114-118.
20. Hudecz, F., et al., The influence of synthetic conditions on the stability of methotrexate-monoclonal antibody conjugates determined by reversed phase high performance liquid chromatography. *Biomedical Chromatography*, 1992. 6(3): p. 128-132.
21. Hurwitz E Fau—Levy, R., et al., The covalent binding of daunomycin and adriamycin to antibodies, with retention of both drug and antibody activities. *Cancer Research*, 1975. 35: p. 1175-1181.
22. Souverain, S., S. Rudaz, and J. L. Veuthey, Restricted access materials and large particle supports for on-line sample preparation: an attractive approach for biological fluids analysis. *Journal of Chromatography B*, 2004. 801(2): p. 141-156.
23. Chari, R. V., et al., Enhancement of the selectivity and antitumor efficacy of a CC-1065 analogue through immunoconjugate formation. *Cancer Res*, 1995. 55(18): p. 4079-84.
24. Greenfield, R. S., et al., Evaluation in vitro of adriamycin immunoconjugates synthesized using an acid-sensitive hydrazone linker. *Cancer Res*, 1990. 50(20): p. 6600-7.
25. Kozak, K. R., et al., Total antibody quantification for MMAE-conjugated antibody-drug conjugates: impact of assay format and reagents. *Bioconjug Chem*, 2013. 24(5): p. 772-9.
26. Liu, M., et al., HPLC method development, validation and impurity characterization for an antitumor Hsp90 inhibitor-PU-H71 (NSC 750424). *J Pharm Biomed Anal*, 2014. 89: p. 34-41.
27. Cohen, S. A., et al., Multiple peak formation in reversed-phase liquid chromatography of papain. *Analytical Chemistry*, 1984. 56(2): p. 217-221.
28. Burton, W. G., et al., Separation of proteins by reversed-phase high-performance liquid chromatography: I. Optimizing the column. *Journal of Chromatography A*, 1988. 443: p. 363-379.
29. Lee, H. M., et al., Microbore high-performance liquid chromatographic determination of cisapride in rat serum samples using column switching. *J Chromatogr B Biomed Sci Appl*, 1999. 727(1-2): p. 213-7.
30. Vega-Morales, T., Z. Sosa-Ferrera, and J. J. Santana-Rodriguez, Development and optimisation of an on-line solid phase extraction coupled to ultra-high-performance liquid chromatography-tandem mass spectrometry methodology for the simultaneous determination of endocrine disrupting compounds in wastewater samples. *J Chromatogr A*, 2012. 1230: p. 66-76.
31. Jeong, C. K., et al., Narrowbore high-performance liquid chromatography for the simultaneous determination of sildenafil and its metabolite UK-103,320 in human plasma using column switching. *J Chromatogr B Biomed Sci Appl*, 2001. 752(1): p. 141-7.
32. Thorson, J. S., et al., Understanding and Exploiting Nature's Chemical Arsenal: The Past, Present and Future of Calicheamicin Research. *Current Pharmaceutical Design*, 2000. 6(18): p. 1841-1879.
33. Clardy, J. and C. Walsh, Lessons from natural molecules. *Nature*, 2004. 432(7019): p. 829-837.
34. Fleming, M. S., et al., A reversed-phase high-performance liquid chromatography method for analysis of monoclonal antibody—maytansinoid immunoconjugates. *Analytical Biochemistry*, 2005. 340(2): p. 272-278.
35. Li, Y., et al., A size exclusion-reversed phase two dimensional-liquid chromatography methodology for stability and small molecule related species in antibody drug conjugates. *J Chromatogr A*, 2015. 1393: p. 81-8.
36. He, Y., et al., On-line coupling of size exclusion chromatography with mixed-mode liquid chromatography for comprehensive profiling of biopharmaceutical drug product. *J Chromatogr A*, 2012. 1262: p. 122-9.
37. Li, Y., et al., Characterization and Stability Study of Polysorbate 20 in Therapeutic Monoclonal Antibody Formulation by Multidimensional Ultrahigh-Performance Liquid Chromatography-Charged Aerosol Detection-Mass *Spectrometry. Analytical Chemistry*, 2014. 86(10): p. 5150-5157.
38. Stoll, D. R., et al., Direct Identification of Rituximab Main Isoforms and Subunit Analysis by Online Selective Comprehensive Two-Dimensional Liquid Chromatography-Mass Spectrometry. *Analytical Chemistry*, 2015. 87(16): p. 8307-8315.
39. Zhang, K., et al., Analysis of pharmaceutical impurities using multi-heartcutting 2D LC coupled with UV-charged aerosol MS detection. *Journal of Separation Science*, 2013. 36(18): p. 2986-2992.
40. Birdsall, R. E., et al., A rapid on-line method for mass spectrometric confirmation of a cysteine-conjugated antibody-drug-conjugate structure using multidimensional chromatography. *mAbs*, 2015: p. 00-00.
41. Lazar, A. C., et al., Analysis of the composition of immunoconjugates using size-exclusion chromatography coupled to mass spectrometry. *Rapid Commun Mass Spectrom,* 2005. 19(13): p. 1806-14.
42. Valliere-Douglass, J., A. Wallace, and A. Balland, Separation of populations of antibody variants by fine tuning of hydrophobic-interaction chromatography operating conditions. *Journal of Chromatography A,* 2008. 1214(1-2): p. 81-89.
43. Valliere-Douglass, J. F., S. M. Hengel, and L. Y. Pan, Approaches to Interchain Cysteine-Linked ADC Characterization by Mass *Spectrometry. Molecular Pharmaceutics,* 2014.
44. Valliere-Douglass, J. F., W. A. McFee, and O. Salas-Solano, Native Intact Mass Determination of Antibodies Conjugated with Monomethyl Auristatin E and F at Interchain Cysteine Residues. *Analytical Chemistry,* 2012. 84(6): p. 2843-2849.
45. Chen, J., et al., Development of a native nanoelectrospray mass spectrometry method for determination of the drug-to-antibody ratio of antibody-drug conjugates. *Anal Chem,* 2013. 85(3): p. 1699-704.
46. Wagner-Rousset, E., et al., Antibody-drug conjugate model fast characterization by LC-MS following IdeS. *mAbs,* 2014. 6(1): p. 173-184.
47. Debaene, F., et al., Innovative Native MS Methodologies for Antibody Drug Conjugate Characterization: High Resolution Native MS and IM-MS for Average DAR and DAR Distribution Assessment. *Analytical Chemistry,* 2014. 86(21): p. 10674-10683.
48. Huang, R. C., et al., Utility of Ion Mobility Mass Spectrometry for Drug-to-Antibody Ratio Measurements in Antibody-Drug Conjugates. *Journal of The American Society for Mass Spectrometry,* 2015: p. 1-4.
49. Janin-Bussat, M. C., et al., Characterization of antibody drug conjugate positional isomers at cysteine residues by peptide mapping LC-MS analysis. *J Chromatogr B Analyt Technol Biomed Life Sci,* 2014. 981-982: p. 9-13.
50. Pascoe, R., J. P. Foley, and A. I. Gusev, Reduction in matrix-related signal suppression effects in electrospray ionization mass spectrometry using on-line two-dimensional liquid chromatography. *Anal Chem,* 2001. 73(24): p. 6014-23.
51. King, R., et al., Mechanistic investigation of ionization suppression in electrospray ionization. *Journal of the American Society for Mass Spectrometry,* 2000. 11(11): p. 942-950.
52. Stoll, D. R., X. Wang, and P. W. Can, Comparison of the practical resolving power of one- and two-dimensional high-performance liquid chromatography analysis of metabolomic samples. *Anal Chem,* 2008. 80(1): p. 268-78.
53. Francisco, J. A., et al., cAC10-vcMMAE, an anti-CD30-monomethyl auristatin E conjugate with potent and selective antitumor activity. *Blood,* 2003. 102(4): p. 1458-1465.
54. Green, J. M., Peer Reviewed: A Practical Guide to Analytical Method Validation. *Analytical Chemistry,* 1996. 68(9): p. 305A-309A.
55. Singtoroj, T., et al., A new approach to evaluate regression models during validation of bioanalytical assays. *J Pharm Biomed Anal,* 2006. 41(1): p. 219-27.
56. Wakankar, A., et al., Analytical methods for physicochemical characterization of antibody drug conjugates. *mAbs,* 2011. 3(2): p. 161-172.

What is claimed is:

1. A method for analyzing antibody-drug conjugate compounds, said method comprising:
   (i) providing a sample comprising an antibody-drug conjugate compound, unconjugated drug compound, and a linker molecule;
   (ii) exposing the sample to a solid phase extraction column comprising a mixed mode stationary phase;
   (iii) diluting an eluting solvent from the solid phase extraction column;
   (iv) exposing the sample to a reverse phase chromatography column comprising hydrophobic stationary phase;
   (v) trapping a portion of the unconjugated drug compound and/or the linker molecule with a stationary phase either prior to the solid phase extraction column or between the solid phase extraction column and the reverse phase chromatography column;
   (vi) separating the antibody-drug conjugate compound, the unconjugated drug compound and the linker molecule in the sample;
   (vii) detecting each of the antibody-drug conjugate compound, the unconjugated drug compound and the linker molecule in the sample using a mass spectrometry; and
   (viii) quantifying an amount of unconjugated drug compound in the sample.

2. The method of claim 1, wherein the mass spectrometry is used to establish a mass to charge ratio of each of the antibody-drug conjugate compound, the unconjugated drug compound and the linker molecule in the sample.

3. The method of claim 1, further comprising a step of adjusting acid concentration to retain the unconjugated drug compound in either the solid phase extraction column or the reverse phase chromatography column.

4. The method of claim 1, wherein the mixed mode stationary phase comprises a hydrophobic solid phase extraction resin interspersed with anion exchange functional groups.

5. The method of claim 1, wherein the linker molecule comprises a non-cleavable linker, a pH labile linker, or combination thereof.

* * * * *